(12) United States Patent
Miura et al.

(10) Patent No.: US 12,060,562 B2
(45) Date of Patent: Aug. 13, 2024

(54) PROTEIN EXPRESSION SYSTEM IN PLANT CELL AND USE THEREOF

(71) Applicant: University of Tsukuba, Tsukuba (JP)

(72) Inventors: Kenji Miura, Tsukuba (JP); Hiroshi Ezura, Tsukuba (JP); Ken Hoshikawa, Tsukuba (JP)

(73) Assignee: University of Tsukuba, Tsukuba (JP)

( * ) Notice: Subject to any disclaimer, the term of this patent is extended or adjusted under 35 U.S.C. 154(b) by 948 days.

(21) Appl. No.: 16/603,741

(22) PCT Filed: Mar. 6, 2018

(86) PCT No.: PCT/JP2018/008512
§ 371 (c)(1),
(2) Date: Oct. 8, 2019

(87) PCT Pub. No.: WO2018/220929
PCT Pub. Date: Dec. 6, 2018

(65) Prior Publication Data
US 2021/0108218 A1    Apr. 15, 2021

(30) Foreign Application Priority Data

May 31, 2017   (JP) ................................ 2017-107965

(51) Int. Cl.
*C12N 15/82* (2006.01)
(52) U.S. Cl.
CPC ..... *C12N 15/8205* (2013.01); *C12N 15/8251* (2013.01)
(58) Field of Classification Search
None
See application file for complete search history.

(56) References Cited

U.S. PATENT DOCUMENTS

| 2014/0208458 A1 | 7/2014 | Takatsuji et al. |
| 2015/0368660 A1 | 12/2015 | Mason et al. |
| 2016/0281102 A1 | 9/2016 | Tanaka et al. |

FOREIGN PATENT DOCUMENTS

| JP | 2016-182045 A | 10/2016 | | |
| WO | WO-2013/192278 A1 | 12/2013 | | |
| WO | WO-2013192278 A1 | * 12/2013 | ......... | C12N 15/8203 |
| WO | WO-2014/062036 A1 | 4/2014 | | |

OTHER PUBLICATIONS

Diamos et al. (Frontiers in Plant Science, vol. 27, pp. 1-14, Published 2016).*
Tom et al. (Genome Biology, vol. 16, pp. 1-14 Published 2015).*
Bates et al. (Plant Cell, 26:151-153, 2014).*
Qiang Chen et al. ( Human Vaccines, 7:331-338. 2011).*
Gutierrez et al. (Veterinary Microbiology, 98:111-119, 2004).*
Gutierrez ( CMLS Cellular and Molecular Life Sciences, 56: 313-329, 1999).*
Diamons et al. (Frontiers in Plant Science, 7:1-15, Published Feb. 24, 2016).*
Nagaya et al. (Plant Cell Physiol., 51:328-332, 2010).*
Cermak et al. (Genome Biology, 16:1-14, Published 2015).*
Baltes et al. (The Plant Cell, 26:151-16, 2014).*
Chen et al. (Human Vaccines, 7::331-338, 2011).*
Beyene et al. (Plant Cell Rep. 30 13-25, 2011).*
Coll Anna et al., "Rule-Based Design of Plant Expression Vectors Using GenoCAD", PLOS One, vol. 10, No. 7, Jul. 6, 2015, p. e0132502, XP055829449, DOI: 10.1371 /journal.pone.0132502.
European Office Action mailed Aug. 13, 2021 for the corresponding European Patent Application No. 18810050.7.
Tomas Cermak et al., "High-frequency, precise modification of the tomato genome", *Genome Biology*, Nov. 6, 2015, XP055413252, DOI: 10.1186/s13059-015-0796-9, vol. 16, No. 1.
Baltes NJ et al., "DNA replicons for plant genome engineering", *The Plant Cell, American Society of Plant Biologists, US*, Jan. 1, 2014, pp. 151-163, XP002752140, ISSN: 1040-4651, DOI: 10.1105/TPC.113.119792, vol. 26, No. 1.
Qiang Chen et al., "Geminiviral vectors based on bean yellow dwarf virus for production of vaccine antigens and monoclonal antibodies in plants", *Human Vaccines*, Mar. 1, 2011, pp. 331-338, XP055750608, US, ISSN: 1554-8600, DOI: 10.4161/hv.7.3.14262, vol. 7, No. 3.
Pooja Saxena et al., "Improved foreign gene expression in plants using a virus-encoded suppressor of RNA silencing modified to be developmentally harmless", *Plant Biotechnology Journal*, Nov. 16, 2010, pp. 703-712, XP055750698, GB, ISSN: 1467-7644, DOI: 10.1111/j.1467-7652.2010.00574.x, vol. 9, No. 6.
European Search Report mailed Nov. 27, 2020 for the corresponding European Patent Application No. 18810050.7.
Japanese Office Action mailed Dec. 8, 2020 for the corresponding Japanese Patent Application No. 2019-521960.
Marillonnet S., et al., "Systemic Agrobacterium tumefaciens-mediated transfection of viral replicons for efficient transient expression in plants", *Nat. Bioteclmol.*, Jun. 2005, pp. 718-723, vol. 23, No. 6.
Moon K. B., et al., "Overexpression and self-assembly of virus-like particles in *Nicotiana benthamiana* by a single-vector DNA replicon system", *Appl. Microbiol. Bioteclmol.*, Jun. 26, 2014, pp. 8281-8290, vol. 98, No. 19.
Diamos A.G. et al., "5' and 3' Untranslated Regions Strongly Enhance Performance of Geminiviral Replicons in Nicotiana benthamiana Leaves", *Front. Plant Sci.*, Feb. 2016, vol. 7, Article 200, doi: 10.3389/fpls.2016.00200.

(Continued)

*Primary Examiner* — Vinod Kumar
(74) *Attorney, Agent, or Firm* — Leason Ellis LLP; Melvin C. Garner; Mitsuhiro Haraguchi

(57) ABSTRACT

An expression system is provided, including a first nucleic acid fragment containing a long intergenic region (LIR) derived from geminivirus, a small intergenic region (SIR) derived from geminivirus, and an expression cassette of a target protein linked between the LIR and the SIR and a second nucleic acid fragment containing an expression cassette of a Rep/RepA protein derived from geminivirus, in which the expression cassette of the target protein includes a promoter, a nucleic acid fragment encoding the target protein, and two or more linked terminators in this order.

9 Claims, 9 Drawing Sheets
(3 of 9 Drawing Sheet(s) Filed in Color)
Specification includes a Sequence Listing.

(56) References Cited

OTHER PUBLICATIONS

Nagaya, S. et al., "The HSP Terminator of *Arabidopsis thaliana* Increases Gene Expression in Plant Cells", *Plant Cell Physiol.*, 2010, pp. 328-332, vol. 51.

Luo, Z. et al., "Improperly Terminated, Unpolyadenylated mRNA of Sense Transgenes Is Targeted by RDR6-Mediated RNA Silencing in *Arabidopsis*", *Plant Cell*, Mar. 2007, pp. 943-958, vol. 19.

Beyene, G. et al., "Unprecedented enhancement of transient gene expression from minimal cassettes using a double terminator", *Plant Cell Rep.*, 2011, vol. 30, pp. 13-25.

Kenji Miura et al., "Improvement of transient expression system for production of recombinant proteins", *Proceedings of the Japanese Society for Plant Cell and Molecular Biology Symposium*, Aug. 20, 2017, pp. 180, vol. 35.

Kenji Miura, "Study for expression of valuable proteins in a mass using plants", *Proceedings of the 2015 Seminar on Grant-Supported Research Findings*, the Asahi Glass Foundation, 2016, vol. 2016, pp. 46-47.

Kenji Miura, "Study for expression of valuable proteins in a mass using plants", *Proceedings of the Seminar on Grant Reported Research Findings*, the Asahi Glass Foundation, Rep. Grant. Res. Asahi Glass Foundation, 2016, vol. 2016, paper No. 25.

T. Yamamoto et al., "Improvement of the transient expression system for production of recombinant proteins in plants", *Scientific Reports*, Mar. 19, 2018, vol. 8, Article No. 4755, doi: 10.1038/s41598-018-23024-y.

International Search Report mailed May 29, 2018 for the corresponding PCT International Patent Application No. PCT/JP2018/008512.

International Preliminary Report on Patentability mailed Apr. 2, 2019 for the corresponding PCT International Application No. PCT/JP2018/008512.

\* cited by examiner

FIG. 3A pBYR2HS-EGFP  pBYR2fp-EGFP
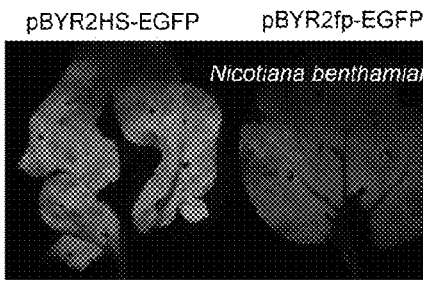
Nicotiana benthamiana

FIG. 3B pBYR2HS-EGFP  pBYR2fp-EGFP
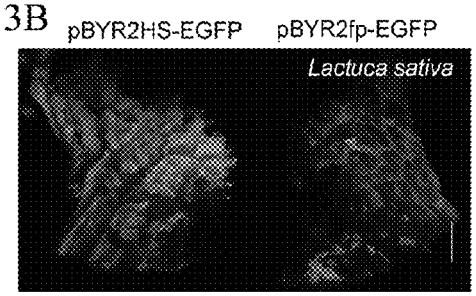
Lactuca sativa

FIG. 3C pBYR2HS-EGFP  pBYR2fp-EGFP
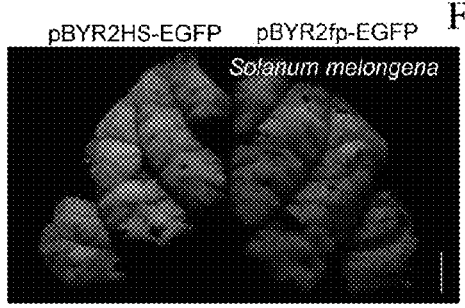
Solanum melongena

FIG. 3D pBYR2HS-EGFP  pBYR2fp-EGFP
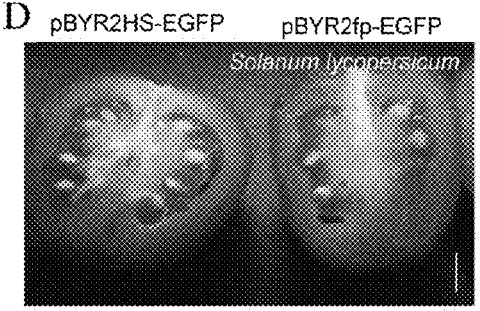
Solanum lycopersicum

FIG. 3E pBYR2HS-EGFP  pBYR2fp-EGFP
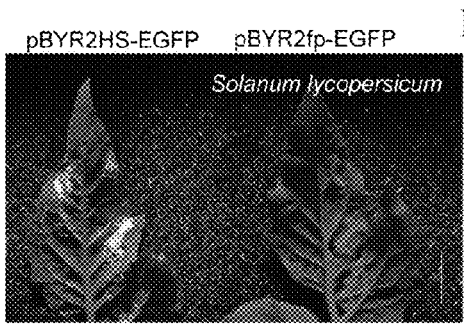
Solanum lycopersicum

FIG. 3F pBYR2HS-EGFP  pBYR2fp-EGFP
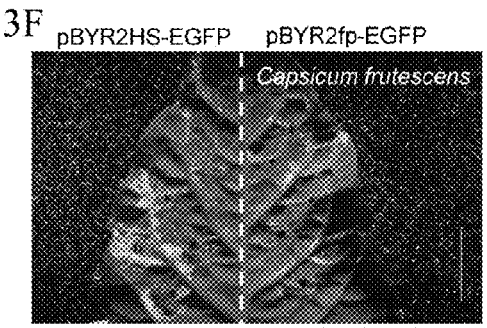
Capsicum frutescens

FIG. 3G pBYR2HS-EGFP  pBYR2fp-EGFP
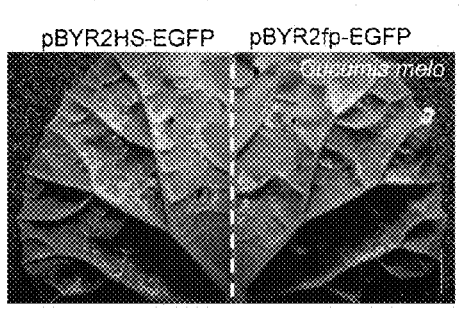
Cucumis melo

FIG. 3H pBYR2HS-EGFP  pBYR2fp-EGFP
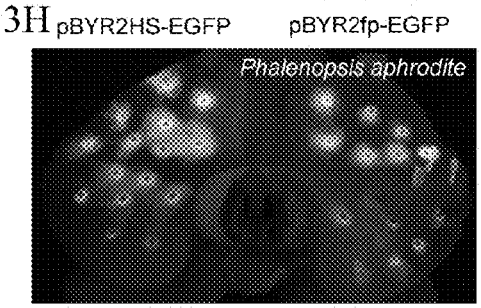
Phalaenopsis aphrodite

FIG. 3I pBYR2HS-EGFP  pBYR2fp-EGFP
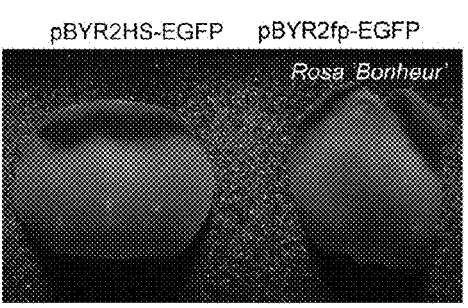
Rosa 'Bonheur'

SEQUENCE LISTING

<160> NUMBER OF SEQ ID NOS: 28

<210> SEQ ID NO 1
<211> LENGTH: 40
<212> TYPE: DNA
<213> ORGANISM: Artificial Sequence
<220> FEATURE:
<223> OTHER INFORMATION: synthesized oligonucleotide named pBYR2fp-EGFP-F

<400> SEQUENCE: 1
ctatttacaa tctagaatgg tgagcaaggg cgaggagctg           40

```
<210> SEQ ID NO 2
<211> LENGTH: 40
<212> TYPE: DNA
<213> ORGANISM: Artificial Sequence
<220> FEATURE:
<223> OTHER INFORMATION: synthesized oligonucleotide named
      EGFP-pBYR2fp-R

<400> SEQUENCE: 2
ccggggatcc tctagttatc cggacttgta cagctcgtcc                          40

<210> SEQ ID NO 3
<211> LENGTH: 38
<212> TYPE: DNA
<213> ORGANISM: Artificial Sequence
<220> FEATURE:
<223> OTHER INFORMATION: synthesized oligonucleotide named pRI201-EGFP-F

<400> SEQUENCE: 3
cactgttgat acatatggtg agcaagggcg aggagctg                            38

<210> SEQ ID NO 4
<211> LENGTH: 45
<212> TYPE: DNA
<213> ORGANISM: Artificial Sequence
<220> FEATURE:
<223> OTHER INFORMATION: synthesized oligonucleotide named EGFP-pRI201-R

<400> SEQUENCE: 4
attcagaatt gtcgacttat ccggacttgt acagctcgtc catgc                    45

<210> SEQ ID NO 5
<211> LENGTH: 41
<212> TYPE: DNA
<213> ORGANISM: Artificial Sequence
<220> FEATURE:
<223> OTHER INFORMATION: synthesized oligonucleotide named
      pBYR2fp-AtADH-F

<400> SEQUENCE: 5
tggagaggac ctcgagtaca tcacaatcac acaaaactaa c                        41

<210> SEQ ID NO 6
<211> LENGTH: 41
<212> TYPE: DNA
<213> ORGANISM: Artificial Sequence
<220> FEATURE:
<223> OTHER INFORMATION: synthesized oligonucleotide named
      pBYR2fp-HSPter-R

<400> SEQUENCE: 6
ccggggatcc tctagaaatt ccttatcttt aatcatattc c                        41

<210> SEQ ID NO 7
<211> LENGTH: 40
<212> TYPE: DNA
<213> ORGANISM: Artificial Sequence
<220> FEATURE:
<223> OTHER INFORMATION: synthesized oligonucleotide named
      pBYR2EE-Ext3-F

<400> SEQUENCE: 7
gtccggataa gtcgacgaag tgacatcaca aagttgaagg                          40

<210> SEQ ID NO 8
<211> LENGTH: 40
```

```
<212> TYPE: DNA
<213> ORGANISM: Artificial Sequence
<220> FEATURE:
<223> OTHER INFORMATION: synthesized oligonucleotide named
      pBYR2EE-Ext3-R

<400> SEQUENCE: 8
ccggggatcc tctagagtca taactgtaga aatgattcca                           40

<210> SEQ ID NO 9
<211> LENGTH: 41
<212> TYPE: DNA
<213> ORGANISM: Artificial Sequence
<220> FEATURE:
<223> OTHER INFORMATION: synthesized oligonucleotide named
      pBYR2H-HSPter-F

<400> SEQUENCE: 9
ataaggaatt tctagttatg aagatgaaga tgaaatattt g                        41

<210> SEQ ID NO 10
<211> LENGTH: 41
<212> TYPE: DNA
<213> ORGANISM: Artificial Sequence
<220> FEATURE:
<223> OTHER INFORMATION: synthesized oligonucleotide named
      pBYR2H-HSPter-R

<400> SEQUENCE: 10
ccggggatcc tctagaaatt ccttatcttt aatcatattc c                        41

<210> SEQ ID NO 11
<211> LENGTH: 44
<212> TYPE: DNA
<213> ORGANISM: Artificial Sequence
<220> FEATURE:
<223> OTHER INFORMATION: synthesized oligonucleotide named HSPter-SIR-F

<400> SEQUENCE: 11
ctagaggatc cccgggcgag tgtacttcaa gtcagttgga aatc                     44

<210> SEQ ID NO 12
<211> LENGTH: 25
<212> TYPE: DNA
<213> ORGANISM: Artificial Sequence
<220> FEATURE:
<223> OTHER INFORMATION: synthesized oligonucleotide named C1-ClaI-C2-R

<400> SEQUENCE: 12
atcatgtaag catcgatgcc tacac                                          25

<210> SEQ ID NO 13
<211> LENGTH: 40
<212> TYPE: DNA
<213> ORGANISM: Artificial Sequence
<220> FEATURE:
<223> OTHER INFORMATION: synthesized oligonucleotide named
      pBYR2T-35Ster-F

<400> SEQUENCE: 13
gtccggataa gtcgacgatc tgtcgatcga caagctcgag                          40

<210> SEQ ID NO 14
<211> LENGTH: 36
<212> TYPE: DNA
<213> ORGANISM: Artificial Sequence
<220> FEATURE:
```

<223> OTHER INFORMATION: synthesized oligonucleotide named
      35Ster-NOster-R

<400> SEQUENCE: 14
gtttgaacga tctaattcgg gggatctgga ttttag                              36

<210> SEQ ID NO 15
<211> LENGTH: 38
<212> TYPE: DNA
<213> ORGANISM: Artificial Sequence
<220> FEATURE:
<223> OTHER INFORMATION: synthesized oligonucleotide named
      35Ster-NOster-F

<400> SEQUENCE: 15
tcccccgaat tagatcgttc aaacatttgg caataaag                            38

<210> SEQ ID NO 16
<211> LENGTH: 41
<212> TYPE: DNA
<213> ORGANISM: Artificial Sequence
<220> FEATURE:
<223> OTHER INFORMATION: synthesized oligonucleotide named
      pBYR2TN-NOster-R

<400> SEQUENCE: 16
ccggggatcc tctagagatc tagtaacata gatgacaccg c                        41

<210> SEQ ID NO 17
<211> LENGTH: 40
<212> TYPE: DNA
<213> ORGANISM: Artificial Sequence
<220> FEATURE:
<223> OTHER INFORMATION: synthesized oligonucleotide named
      pBYR2HS-35Ster-R

<400> SEQUENCE: 17
ccggggatcc tctagataat tcggggatc tggattttag                           40

<210> SEQ ID NO 18
<211> LENGTH: 43
<212> TYPE: DNA
<213> ORGANISM: Artificial Sequence
<220> FEATURE:
<223> OTHER INFORMATION: synthesized oligonucleotide named
      pBYR2HS-35Ster-F

<400> SEQUENCE: 18
ataaggaatt tctaggatct gtcgatcgac aagctcgagt ttc                      43

<210> SEQ ID NO 19
<211> LENGTH: 250
<212> TYPE: DNA
<213> ORGANISM: Arabidopsis thaliana

<400> SEQUENCE: 19
ttatgaagat gaagatgaaa tatttggtgt gtcaaataaa aagctagctt gtgtgcttaa    60
gtttgtgttt ttttcttggc ttgttgtgtt atgaatttgt ggcttttttct aatattaaat   120 gaatgtaaga tctcattata atgaataaac aaatgtttct ataatccatt gtgaatgttt    180
tgttggatct cttcgcatat aactactgta tgtgctatgg tatggactat ggaatatgat    240
taaagataag                                                          250

<210> SEQ ID NO 20

```
<211> LENGTH: 731
<212> TYPE: DNA
<213> ORGANISM: Nicotiana tabacum

<400> SEQUENCE: 20
gaagtgacat cacaaagttg aaggtaataa agccaaatta attaagacat tttcataatg    60
atgtcaagaa tgcaaagcaa attgcataac tgcctttatg caaaacatta atataatata   120
aattataaag aactgcgctc tctgcttctt attttcttag cttcatttat tagtcactag   180
ctgttcagaa ttttcagtat cttttgatat tactaagaac ctaatcacac aatgtatatt   240
cttatgcagg aaaagcagaa tgctgagcta aagaaaggc ttttccatt ttcgagagac     300 aatgagaaaa gaagaagaag aagaagaaga agaagaagaa gaaagagta ataataaag     360 ccccacagga ggcgaagttc ttgtagctcc atgttatcta agttattgat attgtttgcc   420
ctatatttta tttctgtcat tgtgtatgtt ttgttcagtt tcgatctcct tgcaaaatgc   480
agagattatg agatgaataa actaagttat attattatac gtgttaatat tctcctcctc   540
tctctagcta gcctttttgtt ttctcttttt cttatttgat tttctttaaa tcaatccatt   600
ttaggagagg gccagggagt gatccagcaa acatgaaga ttagaagaaa cttccctctt    660 tttttttcctg aaaacaattt aacgtcgaga tttatctctt tttgtaatgg aatcatttct  720
acagttatga c                                                        731

<210> SEQ ID NO 21
<211> LENGTH: 209
<212> TYPE: DNA
<213> ORGANISM: Cauliflower mosaic virus

<400> SEQUENCE: 21
gatctgtcga tcgacaagct cgagtttctc cataataatg tgtgagtagt tcccagataa    60
gggaattagg gttcctatag ggtttcgctc atgtgttgag catataagaa accctttagta  120 tgtatttgta tttgtaaaat acttctatca ataaaatttc taattcctaa aaccaaaatc   180
cagtactaaa atccagatcc cccgaatta                                     209

<210> SEQ ID NO 22
<211> LENGTH: 253
<212> TYPE: DNA
<213> ORGANISM: Cauliflower mosaic virus

<400> SEQUENCE: 22
gatcgttcaa acatttggca ataaagtttc ttaagattga atcctgttgc cggtcttgcg    60
atgattatca tataatttct gttgaattac gttaagcatg taataattaa catgtaatgc   120
atgacgttat ttatgagatg gttttttatg attagagtcc cgcaattata catttaatac   180
gcgatagaaa acaaaatata gcgcgcaaac taggataaat tatcgcgcgc ggtgtcatct   240
atgttactag atc                                                      253

<210> SEQ ID NO 23
<211> LENGTH: 341
<212> TYPE: DNA
<213> ORGANISM: Unknown
<220> FEATURE:
<223> OTHER INFORMATION: Geminiviridae

<400> SEQUENCE: 23
gctctagcag aaggcatgtt gttgtgactc cgaggggttg cctcaaactc tatcttataa    60
ccggcgtgga ggcatggagg caagggcatt ttggtaattt aagtagttag tggaaaatga   120
```

```
cgtcatttac ttaaagacga agtcttgcga caagggggc ccacgccgaa ttttaatatt      180
accggcgtgg ccccaccta tcgcgagtgc tttagcacga gcggtccaga tttaaagtag      240
aaaagttccc gcccactagg gttaaaggtg ttcacactat aaaagcatat acgatgtgat      300
ggtatttgat ggagcgtata ttgtatcagg tatttccgtc g                         341

<210> SEQ ID NO 24
<211> LENGTH: 200
<212> TYPE: DNA
<213> ORGANISM: Unknown
<220> FEATURE:
<223> OTHER INFORMATION: Geminiviridae

<400> SEQUENCE: 24
cgagtgtact tcaagtcagt tggaaatcaa taaaatgatt attttatgaa tatatttcat      60
tgtgcaagta gatagaaatt acatatgtta cataacacac gaaataaaca aaaaaacaca     120
atccaaaaca aacaccccaa acaaaataac actatatata tcctcgtatg aggagaggca    180
cgttcagtga ctcgacgatt                                                 200

<210> SEQ ID NO 25
<211> LENGTH: 1091
<212> TYPE: DNA
<213> ORGANISM: Unknown
<220> FEATURE:
<223> OTHER INFORMATION: Geminiviridae

<400> SEQUENCE: 25
atgccttctg ctagcaagaa cttcagactc caatctaaat atgttttcct tacctacccc      60
aagtgctcat ctcaaagaga tgatttattc cagtttctct gggagaaact cacacccttt     120 cttatttct tccttggtgt tgcttctgag cttcatcaag atggcactac ccactatcat     180
gctcttatcc agcttgataa aaaaccttgt attagggatc cttctttttt cgattttgaa     240
ggaaatcacc ctaatatcca gccagctaga aactctaaac aagtccttga ttacatatca     300
aaggacggag atattaaaac cagaggagat ttccgagatc ataaggtgtc tcctcgcaaa     360
tctgacgcac gatggcgaac tattatccag actgcaacgt ctaaggagga gtatcttgac     420
atgatcaaag aagagtttccc tcatgaatgg gcaacaaagc ttcaatggct ggaatattca     480
gccaacaaat tatttcctcc acaacctgag cagtacgtgt cgcccttcac agaatcagat     540
ctccgctgcc acgaagatct gcacaactgg agagagacgc acctatatca tgtaagcatc     600
gatgcctaca ctttcataca tcctgtctcc tacgatcaag cacaatctga ccttgagtgg     660
atggccgatc taaccaggat gagggaagga ctggggtcag acaccccagc ctctacatct     720
gcggaccaac tcgtaccgga aagaccacct gggctagaaa tctcgggcga cacaactact     780
ggaacgggac catcgacttc accaactacg atgaacacgc cacctataat atcatcgacg     840
acatcccctt caagttcgtc ccattgtgga agcaattaat aggttgccag tctgatttca     900
ctgtcaaccc taaatatgga aaaagaagaa aaataaaagg tgggatccct tctataattc     960
tttgcaatcc tgacgaagac tggatgttat caatgacaag tcaacagaag gattactttg    1020
aagataattg cgtcacccac tatatgtgtg acggggagac ttttttttgct cgggaatcgt    1080 cgagtcactg a                                                         1091

<210> SEQ ID NO 26
<211> LENGTH: 186
<212> TYPE: DNA
```

<213> ORGANISM: Agrobacterium tumefaciens

<400> SEQUENCE: 26

```
ggggtcataa cgtgactccc ttaattctcc gctcatgatc agattgtcgt ttcccgcctt    60
cagtttaaac tatcagtgtt tgacaggata tattggcggg taaacctaag agaaaagagc   120
gtttattaga ataatcggat atttaaaagg gcgtgaaaag gtttatccgt tcgtccattt   180
gtatgt                                                              186
```

<210> SEQ ID NO 27
<211> LENGTH: 181
<212> TYPE: DNA
<213> ORGANISM: Agrobacterium tumefaciens

<400> SEQUENCE: 27

```
tgatgggctg cctgtatcga gtggtgattt tgtgccgagc tgccggtcgg ggagctgttg    60
gctggctggt ggcaggatat attgtggtgt aaacaaattg acgcttagac aacttaataa   120
cacattgcgg acgtttttaa tgtactgggg tggttttctc tttcaccagt gagacgggca   180
a                                                                   181
```

<210> SEQ ID NO 28
<211> LENGTH: 15510
<212> TYPE: DNA
<213> ORGANISM: Artificial Sequence
<220> FEATURE:
<223> OTHER INFORMATION: synthesized vector named pBYR2HS-EGFP
<220> FEATURE:
<221> NAME/KEY: misc_feature
<222> LOCATION: (1651)..(1651)
<223> OTHER INFORMATION: n is a, c, g, or t
<220> FEATURE:
<221> NAME/KEY: misc_feature
<222> LOCATION: (1660)..(1660)
<223> OTHER INFORMATION: n is a, c, g, or t
<220> FEATURE:
<221> NAME/KEY: misc_feature
<222> LOCATION: (1686)..(1686)
<223> OTHER INFORMATION: n is a, c, g, or t

<400> SEQUENCE: 28

```
tgatgggctg cctgtatcga gtggtgattt tgtgccgagc tgccggtcgg ggagctgttg    60
gctggctggt ggcaggatat attgtggtgt aaacaaattg acgcttagac aacttaataa   120
cacattgcgg acgtttttaa tgtactgggg tggttttctc tttcaccagt gagacgggca   180
acagctgatt gcccttcacc gcctggccct gagagagttg cagcaagcgg tccacgctgg   240
tttgccccag caggcgaaaa tcctgtttga tggtggttcc gaaatcggca aaatccctta   300
taaatcaaaa gaatagcccg agatagggtt gagtgttgtt ccagtttgga acaagagtcc   360
actattaaag aacgtggact ccaacgtcaa agggcgaaaa accgtctatc agggcgatgg   420
cccactacgt gaaccatcac ccaaatcaag ttttttgggg tcgaggtgcc gtaaagcact   480
aaatcggaac cctaaaggga gcccccgatt tagagcttga cggggaaagc cggcgaacgt   540
ggcgagaaag gaagggaaga agcgaaagg agcggcgcc attcaggctg cgcaactgtt   600
gggaagggcg atcgccgatc tagtaacata gatgacaccg cgcgcgataa tttatcctag   660
tttgcgcgct atattttgtt ttctatcgcg tattaaatgt ataattgcgg gactctaatc   720
ataaaaaccc atctcataaa taacgtcatg cattacatgt taattattac atgcttaacg   780
taattcaaca gaaattatat gataatcatc gcaagaccgg caacaggatt caatcttaag   840
aaactttatt gccaaatgtt tgaacgatct gcttactcgc cttcttttc gaaggtttga   900
```

```
gtaccttcag ggcatcctct tgatacatta ctttccactt cgattggggc aagctgtagc    960
agttcttgct tagaccgaat tgccatctca cagagatgct gaagagttcg cgaccctcca   1020
gaaacggtga tactaactcc tcgaaaccga atactatagg tacatccgat ctggtcgaaa   1080
ccgaaaaatc gagatgctgc atagttaacc gaatctcccg tccaagatcc aaggactctg   1140
tgcagtgaag cttccgtcct gtcgtatctg agatatctct taaatacaac tttcccgaaa   1200
ccccagcttt ccttgaaacc aaggggatta tcttgattcg aattcgtctc atcgttatgt   1260
agccgccact cagtccaact cggactttcg tcaggaagtt tgaagggaga agttgtacct   1320
cctgatcctc catcccaacg ttcactgtta gcttgttccc tagcgtcgtt tccttgtata   1380
gctcgttcca tggctatcgt tcgtaaatgg tgaaaatttt cagaaaattg cttttgcttt   1440
aaaagaaatg atttaaattg ctgcaataga agtagaatgc ttgattgctt gagattcgtt   1500
tgttttgtat atgttgtgtt gagaattaat tcccctcgac tagagtcgag atctggattg   1560
agagtgaata tgagactcta attggatacc gaggggaatt tatggaacgt cagtggagca   1620
ttttgacaa gaaatatttg ctagctgata ntgaccttan gcgactttg aacgcgcaat    1680
aatggnttct gacgtatgtg cttagctcat taaactccag aaacccgcgg ctgagtggct   1740
ccttcaacgt tgcggttctg tcagttccaa acgtaaaacg gcttgtcccg cgtcatcggc   1800
gggggtcata acgtgactcc cttaattctc cgctcatgat cttgatcccc tgcgccatca   1860
gatccttggc ggcaagaaag ccatccagtt tactttgcag ggcttcccaa ccttaccaga   1920
gggcgcccca gctggcaatt ccggttcgct tgctgtccat aaaaccgccc agtctagcta   1980
tcgccatgta agcccactgc aagctacctg cttctctttt gcgcttgcgt tttcccttgt   2040
ccagatagcc cagtagctga cattcatccg gggtcagcac cgtttctgcg gactggcttt   2100
ctacgtgttc cgcttccttt agcagccctt gcgccctgag tgcttgcggc agcgtgaagc   2160
tggcgcgccg ctctagcaga aggcatgttg ttgtgactcc gaggggttgc ctcaaactct   2220
atcttataac cggcgtggag gcatggaggc aagggcattt tggtaattta agtagttagt   2280
ggaaaatgac gtcatttact taaagacgaa gtcttgcgac aagggggggcc cacgccgaat   2340
tttaatatta ccggcgtggc cccaccttat cgcgagtgct ttagcacgag cggtccagat   2400
ttaaagtaga aaagttcccg cccactaggg ttaaaggtgt tcacactata aaagcatata   2460
cgatgtgatg gtatttgatg gagcgtatat tgtatcaggt atttccgtcg gatacgaatt   2520
attcgtacga ccctcctgca ggtcaacatg gtggagcacg acacacttgt ctactccaaa   2580
aatatcaaag atacagtctc agaagaccaa agggcaattg agacttttca acaaaggta   2640
atatccggaa acctcctcgg attccattgc ccagctatct gtcactttat tgtgaagata   2700
gtggaaaagg aaggtggctc ctacaaatgc catcattgcg ataaaggaaa ggccatcgtt   2760
gaagatgcct ctgccgacag tggtcccaaa gatggacccc cacccacgag gagcatcgtg   2820
gaaaaagaag acgttccaac cacgtcttca aagcaagtgg attgatgtga acatggtg   2880
gagcacgaca cacttgtcta ctccaaaaat atcaaagata cagtctcaga agaccaaagg   2940
gcaattgaga cttttcaaca aagggtaata tccggaaacc tcctcggatt ccattgccca   3000
gctatctgtc actttattgt gaagatagtg gaaaggaag gtggctccta caaatgccat   3060
cattgcgata aaggaaaggc catcgttgaa gatgcctctg ccgacagtgg tcccaaagat   3120
ggaccccac ccacgaggag catcgtgaa aagaagacg ttccaaccac gtcttcaaag   3180
caagtggatt gatgtgatat ctccactgac gtaagggatg acgcacaatc ccactatcct   3240
```

-continued

```
tcgcaagacc cttcctctat ataaggaagt tcatttcatt tggagaggac ctcgagtaca    3300
tcacaatcac acaaaactaa caaaagatca aaagcaagtt cttcactgtt gatacatatg    3360
gtgagcaagg gcgaggagct gttcaccggg gtggtgccca tcctggtcga gctggacggc    3420
gacgtaaacg gccacaagtt cagcgtgtcc ggcgagggcg agggcgatgc cacctacggc    3480
aagctgaccc tgaagttcat ctgcaccacc ggcaagctgc ccgtgccctg gcccaccctc    3540
gtgaccaccc tgacctacgg cgtgcagtgc ttcagccgct accccgacca catgaagcag    3600
cacgacttct tcaagtccgc catgcccgaa ggctacgtcc aggagcgcac catcttcttc    3660
aaggacgacg gcaactacaa gacccgcgcc gaggtgaagt tcgagggcga caccctggtg    3720
aaccgcatcg agctgaaggg catcgacttc aaggaggacg gcaacatcct ggggcacaag    3780
ctggagtaca actacaacag ccacaacgtc tatatcatgg ccgacaagca gaagaacggc    3840
atcaaggtga acttcaagat ccgccacaac atcgaggacg gcagcgtgca gctcgccgac    3900
cactaccagc agaacacccc catcggcgac ggccccgtgc tgctgcccga caaccactac    3960
ctgagcaccc agtccgccct gagcaaagac cccaacgaga gcgcgatca catggtcctg    4020 ctggagttcg tgaccgccgc cgggatcact ctcggcatgg acgagctgta caagtccgga    4080
taagtcgaca attctgaatc aacaactctc ctggcgcacc atcgtcggct acagcctcgg    4140
gaattgctac cgagctctta tgaagatgaa gatgaaatat ttggtgtgtc aaataaaaag    4200
ctagcttgtg tgcttaagtt tgtgtttttt tcttggcttg ttgtgttatg aatttgtggc    4260
tttttctaat attaaatgaa tgtaagatct cattataatg aataaacaaa tgtttctata    4320
atccattgtg aatgttttgt tggatctctt cgcatataac tactgtatgt gctatggtat    4380
ggactatgga atatgattaa agataaggaa tttctagagg atccccgggt accgagctcg    4440
aagtgacatc acaagttga aggtaataaa gccaaattaa ttaagacatt ttcataatga    4500
tgtcaagaat gcaaagcaaa ttgcataact gcctttatgc aaaacattaa tataatataa    4560
attataaaga actgcgctct ctgcttctta ttttcttagc ttcatttatt agtcactagc    4620
tgttcagaat tttcagtatc ttttgatatt actaagaacc taatcacaca atgtatattc    4680
ttatgcagga aaagcagaat gctgagctaa agaaaggct ttttccattt tcgagagaca    4740
atgagaaaag aagaagaaga agaagaagaa gaagaagaag aaaagagtaa ataataaagc    4800
cccacaggag gcgaagttct tgtagctcca tgttatctaa gttattgata ttgtttgccc    4860
tatattttat ttctgtcatt gtgtatgttt tgttcagttt cgatctcctt gcaaaatgca    4920
gagattatga gatgaataaa ctaagttata ttattatacg tgttaatatt ctcctcctct    4980
ctctagctag cctttttgttt tctctttttc ttatttgatt ttcttttaaat caatccattt    5040 taggagaggg ccagggagtg atccagcaaa acatgaagat tagaagaaac ttccctcttt    5100
tttttcctga aaacaattta acgtcgagat ttatctcttt ttgtaatgga atcatttcta    5160
cagttatgac gaattccgag tgtacttcaa gtcagttgga aatcaataaa atgattattt    5220
tatgaatata tttcattgtg caagtagata gaaattacat atgttacata acacacgaaa    5280
taaacaaaaa aacacaatcc aaaacaaaca ccccaaacaa aataacacta tatatatcct    5340
cgtatgagga gaggcacgtt cagtgactcg acgattcccg agcaaaaaaa gtctccccgt    5400
cacacatata gtgggtgacg caattatctt caaagtaatc cttctgttga cttgtcattg    5460
ataacatcca gtcttcgtca ggattgcaaa gaattataga agggatccca ccttttattt    5520
tcttcttttt tccatatttta gggttgacag tgaaatcaga ctgcaacct attaattgct    5580 tccacaatgg gacgaacttg aaggggatgt cgtcgatgat attataggtg gcgtgttcat    5640
```

```
cgtagttggt gaagtcgatg gtcccgttcc agtagttgtg tcgcccgaga cttctagccc    5700
aggtggtctt tccggtacga gttggtccgc agatgtagag gctggggtgt ctgaccccag    5760
tccttccctc atcctggtta gatcggccat ccactcaagg tcagattgtg cttgatcgta    5820
ggagacagga tgtatgaaag tgtaggcatc gatgcttaca tgatataggt gcgtctctct    5880
ccagttgtgc agatcttcgt ggcagcggag atctgattct gtgaagggcg acacgtactg    5940
ctcaggttgt ggaggaaata atttgttggc tgaatattcc agccattgaa gctttgttgc    6000
ccattcatga gggaactctt ctttgatcat gtcaagatac tcctccttag acgttgcagt    6060
ctggataata gttcgccatc gtgcgtcaga tttgcgagga cacccttat gatctcggaa     6120 atctcctctg gttttaatat ctccgtcctt tgatatgtaa tcaaggactt gtttagagtt    6180
tctagctggc tggatattag ggtgatttcc ttcaaaatcg aaaaagaag gatccctaat     6240 acaaggtttt ttatcaagct ggataagagc atgatagtgg gtagtgccat cttgatgaag    6300
ctcagaagca acaccaagga agaaaataag aaaaggtgtg agtttctccc agagaaactg    6360
gaataaatca tctctttgag atgagcactt ggggtaggta aggaaaacat atttagattg    6420
gagtctgaag ttcttgctag cagaaggcat gttgttgtga ctccgagggg ttgcctcaaa    6480
ctctatctta taaccggcgt ggaggcatgg aggcaagggc attttggtaa tttaagtagt    6540
tagtggaaaa tgacgtcatt tacttaaaga cgaagtcttg cgacaagggg ggcccacgcc    6600 gaatttaat attaccggcg tggccccacc ttatcgcgag tgctttagca cgagcggtcc     6660
agatttaaag tagaaaagtt cccgcccact agggttaaag gtgttcacac tataaaagca    6720
tatacgatgt gatggtattt gatggagcgt atattgtatc aggtatttcc gtcggatacg    6780
aattattcgt acggccggac cggtccccta ggccggccaa ttcgagatcg gccgcggctg    6840
agtggctcct tcaatcgttg cggttctgtc agttccaaac gtaaacggc ttgtcccgcg     6900 tcatcggcgg gggtcataac gtgactccct taattctccg ctcatgatca gattgtcgtt    6960
tcccgccttc agtttaaact atcagtgttt gacaggatat attggcgggt aaacctaaga    7020
gaaaagagcg tttattagaa taatcggata tttaaagggg cgtgaaaagg tttatccgtt    7080
cgtccatttg tatgtgcatg ccaaccacag ggttccccag atctggcgcc ggccagcgag    7140
acgagcaaga ttggccgccg cccgaaacga tccgacagcg cgcccagcac aggtgcgcag    7200
gcaaattgca ccaacgcata cagcgccagc agaatgccat agtgggcggt gacgtcgttc    7260
gagtgaacca gatcgcgcag gaggcccggc agcaccggca taatcaggcc gatgccgaca    7320
gcgtcgagcg cgacagtgct cagaattacg atcaggggta tgttgggttt cacgtctggc    7380
ctccggacca gcctccgctg gtccgattga acgcgcggat tctttatcac tgataagttg    7440
gtggacatat tatgtttatc agtgataaag tgtcaagcat gacaaagttg cagccgaata    7500
cagtgatccg tgccgccctg gacctgttga acgaggtcgg cgtagacggt ctgacgacac    7560
gcaaactggc ggaacggttg ggggttcagc agccggcgct ttactggcac ttcaggaaca    7620
agcgggcgct gctcgacgca ctggccgaag ccatgctggc ggagaatcat acgcattcgg    7680
tgccgagagc cgacgacgac tggcgctcat ttctgatcgg gaatgcccgc agcttcaggc    7740
aggcgctgct cgcctaccgc gatggcgcgc catccatgc cggcacgcga ccgggcgcac    7800
cgcagatgga aacggccgac gcgcagcttc gcttcctctg cgaggcgggt ttttcggccg    7860
gggacgccgc caatgcgctg atgacaatca gctacttcac tgttggggcc gtgcttgagg    7920
agcaggccgg cgacagcgat gccggcgagc gcggcggcac cgttgaacag gctccgctct    7980
```

```
cgccgctgtt gcgggccgcg atagacgcct tcgacgaagc cggtccggac gcagcgttcg    8040
agcagggact cgcggtgatt gtcgatggat tggcgaaaag gaggctcgtt gtcaggaacg    8100
ttgaaggacc gagaaagggt gacgattgat caggaccgct gccggagcgc aacccactca    8160
ctacagcaga gccatgtaga caacatcccc tcccccttc caccgcgtca gacgcccgta    8220
gcagcccgct acgggctttt tcatgccctg ccctagcgtc caagcctcac ggccgcgctc    8280
ggcctctctg gcggccttct ggcgctcttc cgcttcctcg ctcactgact cgctgcgctc    8340
ggtcgttcgg ctgcggcgag cggtatcagc tcactcaaag gcggtaatac ggttatccac    8400
agaatcaggg gataacgcag gaaagaacat gtgagcaaaa ggccagcaaa aggccaggaa    8460
ccgtaaaaag gccgcgttgc tggcgttttt ccataggctc cgcccccctg acgagcatca    8520
caaaaatcga cgctcaagtc agaggtggcg aaacccgaca ggactataaa gataccaggc    8580
gtttccccct ggaagctccc tcgtgcgctc tcctgttccg accctgccgc ttaccggata    8640
cctgtccgcc tttctccctt cgggaagcgt ggcgctttc cgctgcataa ccctgcttcg    8700
gggtcattat agcgattttt tcggtatatc catcctttt cgcacgatat acaggatttt    8760
gccaaagggt tcgtgtagac tttccttggt gtatccaacg gcgtcagccg gcaggatag    8820 gtgaagtagg cccaccgcg agcgggtgtt ccttcttcac tgtcccttat tcgcacctgg    8880
cggtgctcaa cgggaatcct gctctgcgag gctggccggc taccgccggc gtaacgatg    8940 agggcaagcg gatggctgat gaaaccaagc caaccaggaa gggcagccca cctatcaagg    9000
tgtactgcct tccagacgaa cgaagagcga ttgaggaaaa ggcggcggcg gccggcatga    9060
gcctgtcggc ctacctgctg gccgtcgcc agggctacaa aatcacgggc gtcgtggact    9120
atgagcacgt ccgcgagctg gcccgcatca atggcgacct gggccgcctg gcggcctgc    9180 tgaaactctg gctcaccgac gacccgcgca cggcgcggtt cggtgatgcc acgatcctcg    9240
ccctgctggc gaagatcgaa gagaagcagg acgagcttgg caaggtcatg atgggcgtgg    9300
tccgcccgag ggcagagcca tgacttttt agccgctaaa acggccgggg ggtgcgcgtg    9360
attgccaagc acgtccccat gcgctccatc aagaagagcg acttcgcgga gctggtgaag    9420
tacatcaccg acgagcaagg caagaccgag cgcctttgcg acgctcaccg ggctggttgc    9480
cctcgccgct gggctggcgg ccgtctatgg ccctgcaaac gcgccagaaa cgccgtcgaa    9540
gccgtgtgcg agacaccgcg gccgccggcg ttgtggatac ctcgcggaaa acttggccct    9600
cactgacaga tgaggggcgg acgttgacac ttgaggggcc gactcacccg gcgcggcgtt    9660
gacagatgag gggcaggctc gatttcggcc ggcgacgtgg agctggccag cctcgcaaat    9720
cggcgaaaac gcctgatttt acgcgagttt cccacagatg atgtggacaa gctggggat    9780 aagtgccctg cggtattgac acttgagggg cgcgactact gacagatgag gggcgcgatc    9840
cttgacactt gaggggcaga gtgctgacag atgaggggcg cacctattga catttgaggg    9900
gctgtccaca gcagaaaat ccagcatttg caagggtttc cgcccgtttt tcggccaccg    9960
ctaacctgtc tttaacctg cttttaaacc aatatttata aaccttgttt ttaaccaggg    10020
ctgcgccctg tgcgcgtgac cgcgcacgcc gaaggggggt gcccccctt ctcgaaccct    10080 cccgcccgc taacgcgggc ctcccatccc ccaggggct cgcccctcg gccgcgaacg    10140 gcctcacccc aaaaatggca gcgctggcag tccttgccat tgccgggatc ggggcagtaa    10200
cgggatgggc gatcagcccg agcgcgacgc ccggaagcat tgacgtgccg caggtgctgg    10260
catcgacatt cagcgaccag gtgccgggca gtgagggcgg cggcctgggt ggcggcctgc    10320
ccttcacttc ggccgtcggg gcattcacgg acttcatggc ggggccggca attttacct    10380
```

-continued

```
tgggcattct tggcatagtg gtcgcgggtg ccgtgctcgt gttcgggggt gcgataaacc  10440
cagcgaacca tttgaggtga taggtaagat tataccgagg tatgaaaacg agaattggac  10500
ctttacagaa ttactctatg aagcgccata tttaaaaagc taccaagacg aagaggatga  10560
agaggatgag gaggcagatt gccttgaata tattgacaat actgataaga taatatatct  10620
tttatataga agatatcgcc gtatgtaagg atttcagggg gcaaggcata ggcagcgcgc  10680
ttatcaatat atctatagaa tgggcaaagc ataaaaactt gcatggacta atgcttgaaa  10740
cccaggacaa taaccttata gcttgtaaat tctatcataa ttgggtaatg actccaactt  10800
attgatagtg ttttatgttc agataatgcc cgatgacttt gtcatgcagc tccaccgatt  10860
ttgagaacga cagcgacttc cgtcccagcc gtgccaggtg ctgcctcaga ttcaggttat  10920
gccgctcaat tcgctgcgta tatcgcttgc tgattacgtg cagctttccc ttcaggcggg  10980
attcatacag cggccagcca tccgtcatcc atatcaccac gtcaaagggt gacagcaggc  11040
tcataagacg ccccagcgtc gccatagtgc gttcaccgaa tacgtgcgca acaaccgtct  11100
tccggagact gtcatacgcg taaaacagcc agcgctggcg cgatttagcc ccgacatagc  11160
cccactgttc gtccatttcc gcgcagacga tgacgtcact gcccggctgt atgcgcgagg  11220
ttaccgactg cggcctgagt tttttaagtg acgtaaaatc gtgttgaggc caacgcccat  11280
aatgcgggct gttgcccggc atccaacgcc attcatggcc atatcaatga ttttctggtg  11340
cgtaccgggt tgagaagcgg tgtaagtgaa ctgcagttgc catgttttac ggcagtgaga  11400
gcagagatag cgctgatgtc cggcggtgct tttgccgtta cgcaccaccc cgtcagtagc  11460
tgaacaggag ggacagctga tagacacaga agccactgga gcacctcaaa acaccatca  11520 tacactaaat cagtaagttg gcagcatcac ccataattgt ggtttcaaaa tcggctccgt  11580
cgatactatg ttatacgcca actttgaaaa caactttgaa aaagctgttt tctggtattt  11640
aaggttttag aatgcaagga acagtgaatt ggagttcgtc ttgttataat tagcttcttg  11700
gggtatcttt aaatactgta gaaagagga aggaaataat aaatggctaa atgagaata  11760 tcaccggaat tgaaaaaact gatcgaaaaa taccgctgcg taaaagatac ggaaggaatg  11820
tctcctgcta aggtatataa gctggtggga gaaaatgaaa acctatattt aaaaatgacg  11880
gacagccggt ataaagggac cacctatgat gtggaacggg aaaaggacat gatgctatgg  11940
ctggaaggaa agctgcctgt tccaaaggtc ctgcactttg aacggcatga tggctggagc  12000
aatctgctca tgagtgaggc cgatggcgtc ctttgctcgg aagagtatga agatgaacaa  12060
agccctgaaa agattatcga gctgtatgcg gagtgcatca ggctctttca ctccatcgac  12120
atatcggatt gtccctatac gaatagctta gacagccgct tagccgaatt ggattactta  12180
ctgaataacg atctggccga tgtggattgc gaaaactggg aagaagacac tccatttaaa  12240
gatccgcgcg agctgtatga ttttttaaag acggaaaagc ccgaagagga acttgtcttt  12300
tcccacggcg acctgggaga cagcaacatc tttgtgaaag atggcaaagt aagtggcttt  12360
attgatcttg ggagaagcgg cagggcggac aagtggtatg acattgcctt ctgcgtccgg  12420
tcgatcaggg aggatatcgg ggaagaacag tatgtcgagc tatttttga cttactgggg  12480 atcaagcctg attgggagaa aataaaatat tatattttac tggatgaatt gttttagtac  12540
ctagatgtgg cgcaacgatg ccggcgacaa gcaggagcgc accgacttct tccgcatcaa  12600 gtgtttggc tctcaggccg aggcccacgc caagtatttg gcaagggt cgctggtatt  12660 cgtgcagggc aagattcgga ataccaagta cgagaaggac ggccagacgg tctacgggac  12720
```

```
cgacttcatt gccgataagg tggattatct ggacaccaag gcaccaggcg ggtcaaatca    12780
ggaataaggg cacattgccc cggcgtgagt cggggcaatc ccgcaaggag ggtgaatgaa    12840
tcggacgttt gaccggaagg catacaggca agaactgatc gacgcggggt tttccgccga    12900
ggatgccgaa accatcgcaa gccgcaccgt catgcgtgcg ccccgcgaaa ccttccagtc    12960
cgtcggctcg atggtccagc aagctacggc caagatcgag cgcgacagcg tgcaactggc    13020 tcccectgcc ctgccegcge catcggccgc cgtggagcgt tcgcgtcgtc tcgaacagga    13080
ggcggcaggt ttggcgaagt cgatgaccat cgacacgcga ggaactatga cgaccaagaa    13140
gcgaaaaacc gccggcgagg acctggcaaa acaggtcagc gaggccaagc aggccgcgtt    13200
gctgaaacac acgaagcagc agatcaagga aatgcagctt tccttgttcg atattgcgcc    13260
gtggccggac acgatgcgag cgatgccaaa cgacacggcc cgctctgccc tgttcaccac    13320
gcgcaacaag aaaatcccgc gcgaggcgct gcaaaacaag gtcatttteec acgtcaacaa    13380 ggacgtgaag atcacctaca ccggcgtcga gctgcgggcc gacgatgacg aactggtgtg    13440
gcagcaggtg ttggagtacg cgaagcgcac ccctatcggc gagccgatca ccttcacgtt    13500
ctacgagctt tgccaggacc tgggctggtc gatcaatggc cggtattaca cgaaggccga    13560
ggaatgcctt cgcgcctac aggcgacggc gatgggcttc acgtccgacc gcgttgggca    13620
cctggaatcg gtgtcgctgc tgcaccgctt ccgcgtcctg gaccgtggca agaaaacgtc    13680
ccgttgccag gtcctgatcg acgaggaaat cgtcgtgctg tttgctggcg accactacac    13740
gaaattcata tgggagaagt accgcaagct gtcgccgacg gcccgacgga tgttcgacta    13800
tttcagctcg caccgggagc cgtacccgct caagctggaa accttccgcc tcatgtgcgg    13860
atcggattcc acccgcgtga agaagtggcg cgagcaggtc ggcgaagcct gcgaagagtt    13920
gcgaggcagc ggcctggtgg aacacgcctg ggtcaatgat gacctggtgc attgcaaacg    13980
ctagggcctt gtggggtcag ttccggctgg gggttcagca ccagcgctt tactggcatt    14040 tcaggaacaa gcgggcactg ctcgacgcac ttgcttcgct cagtatcgct cgggacgcac    14100
ggcgcgctct acgaactgcc gataaacaga ggattaaaat tgacaattgt gattaaggct    14160
cagattcgac ggcttggagc ggccgacgtg caggattte gcgagatccg attgtcggcc    14220
ctgaagaaag ctccagagat gttcgggtcc gtttacgagc acgaggagaa aaagcccatg    14280
gaggcgttcg ctgaacggtt gcgagatgcc gtggcattcg gcgcctacat cgacggcgag    14340
atcattgggc tgtcggtctt caaacaggag gacggcccca aggacgctca caaggcgcat    14400
ctgtccggcg ttttcgtgga gcccgaacag cgaggccgag gggtcgccgg tatgctgctg    14460
cgggcgttgc cggcgggttt attgctcgtg atgatcgtcc gacagattcc aacgggaatc    14520
tggtggatgc gcatcttcat cctcggcgca cttaatattt cgctattctg gagcttgttg    14580
tttatttcgg tctaccgcct gccgggcggg gtcgcggcga cggtaggcgc tgtgcagccg    14640
ctgatggtcg tgttcatctc tgccgctctg ctaggtagcc cgatacgatt gatgcggtc    14700 ctgggggcta tttgcggaac tgcggcgtg gcgctgttgg tgttgacacc aaacgcagcg    14760
ctagatcctg tcggcgtcgc agcgggcctg gcggggcgg tttccatggc gttcggaacc    14820
gtgctgaccc gcaagtggca acctcccgtg cctctgctca cctttaccgc ctggcaactg    14880
gcggccggag gacttctgct cgttccagta gctttagtgt ttgatccgcc aatcccgatg    14940
cctacaggaa ccaatgttct cggcctggcg tggctcggcc tgatcggagc gggtttaacc    15000
tacttccttt ggttccgggg gatctcgcga ctcgaaccta cagttgtttc cttactgggc    15060
tttctcagcc ccagatctgg ggtcgatcag ccggggatgc atcaggccga cagtcggaac    15120
```

```
ttcgggtccc cgacctgtac cattcggtga gcaatggata ggggagttga tatcgtcaac   15180
gttcacttct aaagaaatag cgccactcag cttcctcagc ggctttatcc agcgatttcc   15240
tattatgtcg gcatagttct caagatcgac agcctgtcac ggttaagcga gaaatgaata   15300
agaaggctga taattcggat ctctgcgagg gagatgatat ttgatcacag gcagcaacgc   15360
tctgtcatcg ttacaatcaa catgctaccc tccgcgagat catccgtgtt tcaaacccgg   15420
cagcttagtt gccgttcttc cgaatagcat cggtaacatg agcaaagtct gccgccttac   15480
aacggctctc ccgctgacgc cgtcccggac                                    15510
```

PROTEIN EXPRESSION SYSTEM IN PLANT CELL AND USE THEREOF

CROSS-REFERENCE TO RELATED PATENT APPLICATIONS

This application is a U.S. National Phase Application under 35 U.S.C. § 371 of International Patent Application No. PCT/JP2018/008512, filed Mar. 6, 2018, and claims the benefit of priority to Japanese Patent Application No. 2017-107965 filed on May 31, 2017, all of which are incorporated herein by reference in their entirety. The International Application was published in Japanese on Dec. 6, 2018 as International Publication No. WO/2018/220929 under PCT Article 21(2).

The instant application contains a Sequence Listing which has been submitted electronically in ASCII format and is hereby incorporated by reference in its entirety. Said ASCII copy, created on Oct. 7, 2019, is named 06920-008009-US0-SL.txt and is 30,477 bytes in size.

Field of the Invention

The present invention relates to an expression system and use thereof. More specifically, the present invention relates to an expression system, a method for producing a target protein, and an expression vector.

Background of the Invention

Transgenic plants may be used for the purpose of production of recombinant proteins and analysis of protein localization in plants. However, it takes a long time to produce transgenic plants. In addition, expression levels of proteins by transgenic plants tend to be relatively low.

On the other hand, transient expression systems using virus-based vectors may be able to achieve high expression of recombinant proteins in a short time. For example, the magnICON expression system is a tobacco mosaic virus-based virus system developed to achieve a high level of accumulation of recombinant proteins in tobacco leaves (see, for example, Marillonnet S., et al., Systemic *Agrobacterium tumefaciens*-mediated transfection of viral replicons for efficient transient expression in plants., Nat. Biotechnol., 23 (6), 718-723, 2005. Hereafter "Marillonnet S., et al.").

In addition, geminiviruses are known to have a single-stranded circular DNA genome and replicate the genome at a very high copy number by means of a rolling circle DNA replication mechanism. This mechanism has been utilized to increase the expression of proteins in transgenic plants or to increase the expression level of recombinant proteins in transient expression systems (see, for example, Moon K. B., et al., Overexpression and self-assembly of virus-like particles in *Nicotiana benthamiana* by a single-vector DNA replicon system., Appl. Microbiol. Biotechnol., 98 (19), 8281-8290, 2014. Hereafter "Moon K. B., et al.").

Technical Problem

However, the system disclosed in Marillonnet S., et al. is limited to hosts of plants of the genus *Nicotiana*, and may be difficult to apply to other plants. On the other hand, the system disclosed in Moon K. B., et al. may not have sufficient expression levels of proteins. Therefore, an object of the present invention is to provide an expression system that can be applied to plants other than those belonging to the genus *Nicotiana* and exhibits a high expression level of a protein.

SUMMARY OF THE INVENTION

Solution to Problem

The present invention includes the following aspects.

[1] An expression system, including:
a first nucleic acid fragment containing a long intergenic region (LIR) derived from geminivirus, a small intergenic region (SIR) derived from geminivirus, and an expression cassette of a target protein linked between the LIR and the SIR; and
a second nucleic acid fragment containing an expression cassette of a Rep/RepA protein derived from geminivirus,
in which the expression cassette of the target protein includes a promoter, a nucleic acid fragment encoding the target protein, and two or more linked terminators in this order.

[2] The expression system according to [1], in which two of the terminators are linked to each other.

[3] The expression system according to [1] or [2], in which at least one of the terminators is a terminator derived from *Arabidopsis thaliana* heat-shock protein 18.2 gene.

[4] The expression system according to any one of [1] to [3], further including:
a third nucleic acid fragment containing an expression cassette of a gene-silencing suppressor. [5] The expression system according to [4], in which the gene-silencing suppressor is a gene-silencing suppressor P19 derived from tomato bushy stunt virus.

[6] The expression system according to [4] or [5], in which the first nucleic acid fragment, the second nucleic acid fragment, and the third nucleic acid fragment are contained in a single vector.

[7] The expression system according to [6], further including:
a T-DNA right border sequence (RB); and
a T-DNA left border sequence (LB),
in which the first nucleic acid fragment, the second nucleic acid fragment, and the third nucleic acid fragment are present between the RB and the LB.

[8] The expression system according to any one of [1] to [7], in which the geminivirus is a bean yellow dwarf virus.

[9] A method for producing a target protein, including:
a step of introducing the expression system according to any one of [1] to [8] into a plant cell.

[10] An expression vector including:
a first nucleic acid fragment containing an LIR derived from geminivirus, an SIR derived from geminivirus, and an expression cassette linked between the LIR and the SIR,
in which the expression cassette includes a promoter, a multicloning site, and two or more linked terminators in this order.

[11] The expression vector according to [10], in which two of the terminators are linked to each other.

[12] The expression vector according to [10] or [11], in which at least one of the terminators is a terminator derived from *Arabidopsis thaliana* heat-shock protein 18.2 gene.

[13] The expression vector according to any one of [10] to [12], further including:

a second nucleic acid fragment containing an expression cassette of a Rep/RepA protein derived from geminivirus.

[14] The expression vector according to any one of [10] to [13], further including:
a third nucleic acid fragment containing an expression cassette of a gene-silencing suppressor.

[15] The expression vector according to [14], in which the gene-silencing suppressor is a gene-silencing suppressor P19 derived from tomato bushy stunt virus.

[16] The expression vector according to any one of [10] to [15], further including:
a T-DNA right border sequence (RB); and
a T-DNA left border sequence (LB),
in which the first nucleic acid fragment, the second nucleic acid fragment, and the third nucleic acid fragment are present between the RB and the LB.

[17] The expression vector according to any one of [10] to [16], in which the geminivirus is a bean yellow dwarf virus.

Advantageous Effects of Invention

According to the present invention, it is possible to provide an expression system that can be applied to plants other than those belonging to the genus *Nicotiana* and exhibits a high expression level of a protein.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIGS. 3A to 3I are photographs showing the results of observation of fluorescence of expressed EGFP in Experimental Example 1.

DETAILED DESCRIPTION OF THE INVENTION

[Expression System]

Figure 1A:
FIG. 1A is a photograph showing a state in which about 1.2 L of an *Agrobacterium* suspension is placed in a 2 L glass beaker inside a vacuum desiccator in a case of carrying out agroinfiltration.

In one embodiment, the present invention provides an expression system including a first nucleic acid fragment containing an LIR derived from geminivirus, an SIR derived from geminivirus, and an expression cassette of a target protein linked between the LIR and the SIR and a second nucleic acid fragment containing an expression cassette of a Rep/RepA protein derived from geminivirus, in which the expression cassette of a target protein includes a promoter, a nucleic acid fragment encoding the target protein, and two or more linked terminators in this order.

In a case where the expression system of the present embodiment is introduced into a plant, the Rep/RepA protein, which is a replication initiation protein of geminivirus, is expressed from the second nucleic acid fragment. Then, the expression cassette of the target protein linked between LIR and SIR on the first nucleic acid fragment is replicated at a high copy number by the rolling circle DNA replication mechanism of geminivirus. Subsequently, the target protein is expressed at a high expression level from the expression cassette of the target protein replicated at a high copy number.

As will be described later in the Examples, the expression system of the present embodiment can achieve a very high expression level of the target protein by including two or more linked terminators in the expression cassette of the target protein.

The terminator is a base sequence that terminates transcription of DNA into mRNA. The terminator is not particularly limited, and examples thereof include a terminator derived from *Arabidopsis thaliana* heat-shock protein 18.2 gene, a tobacco extensin gene terminator, a cauliflower mosaic virus (CaMV) 35S terminator, and a CaMV NOS terminator. In the expression system of the present embodiment, two or more linked terminators may be terminators of the same base sequence or may be terminators of different base sequences.

The base sequence of the terminator derived from *Arabidopsis thaliana* heat-shock protein 18.2 gene is set forth in SEQ ID NO: 19. In addition, the base sequence of the tobacco extensin gene terminator is set forth in SEQ ID NO: 20. In addition, the base sequence of the CaMV 35S terminator is set forth in SEQ ID NO: 21. In addition, the base sequence of the CaMV NOS terminator is set forth in SEQ ID NO: 22.

The base sequences of these terminators may each have mutations with respect to the base sequences of SEQ ID NOS: 19 to 22, or the base sequences of SEQ ID NOS: 19 to 22 may be partially deleted, as long as they have a function of terminating transcription of DNA into mRNA.

In a case where the base sequence of the terminator has a mutation or deletion with respect to the base sequences of SEQ ID NOS: 19 to 22, each base sequence preferably has, for example, 70% or more sequence identity, more preferably 80% or more sequence identity, still more preferably 90% or more sequence identity, and particularly preferably 95% or more sequence identity, with respect to the base sequences of SEQ ID NOS: 19 to 22, respectively.

Here, the sequence identity of the target base sequence with respect to the reference base sequence can be determined, for example, as follows. First, the reference base sequence and the target base sequence are aligned. Here, each base sequence may include a gap so as to maximize sequence identity. Subsequently, the number of matched bases in the reference base sequence and the target base sequence is calculated, and then the sequence identity can be determined according to the following formula (1).

$$\text{Sequence identity (\%)} = \text{number of matched bases}/\text{total number of bases in target base sequence} \times 100 \quad (1)$$

In the expression system of the present embodiment, the expression cassette of the target protein preferably contains two terminators. As will be described later in the Examples, the expression level of the target protein tends to be higher in a case where the expression cassette of the target protein contains two terminators than in a case where the expression cassette of the target protein contains three or more terminators.

In addition, in the expression system of the present embodiment, it is preferable that at least one of the terminators contained in the expression cassette of the target protein be a terminator derived from *Arabidopsis thaliana* heat-shock protein 18.2 gene.

As will be described later in the Examples, an expression system containing a terminator derived from *Arabidopsis thaliana* heat-shock protein 18.2 gene as the terminator tends to have a high expression level of the target protein.

As will be described later in the Examples, the expression system of the present embodiment can express a target protein of about 3 mg or more per 1 g fresh weight of a plant. This expression level is equivalent to that of the currently commercially available magnICON system.

In addition, as will be described later in the Examples, the magnICON system is limited to hosts of plants of the genus *Nicotiana*, whereas the expression system of the present embodiment can achieve a high expression level of a target protein not only in plants of the genus *Nicotiana* but also in plants other than those belonging to the genus *Nicotiana*. Here, examples of plants other than those belonging to the genus *Nicotiana* include, but are not limited to, solanaceous plants such as tomato, eggplant, and hot pepper; *Asteraceae* plants such as lettuce; cucurbitaceous plants such as melon; and orchidaceous plants such as phalaenopsis orchid.

In the expression system of the present embodiment, the first nucleic acid fragment contains a promoter, a nucleic acid fragment encoding a target protein, and two or more linked terminators in this order.

Any promoter can be used without particular limitation as long as it exhibits transcriptional activity of DNA linked downstream thereof in a host plant cell. Specific examples of the promoter include a cauliflower mosaic virus (CaMV) 35S promoter, a ubiquitin promoter, and a cassava vein mosaic virus (CsVMV) promoter.

The target protein is not particularly limited, and any protein can be expressed. According to the expression system of the present embodiment, proteins can be expressed at low cost as compared to protein expression using animal cells. In addition, the expression system of the present embodiment can be used to express a pollen allergen or the like which is difficult to express in an expression system such as *E. coli*. For this reason, the target protein may be, for example, a pollen allergen.

The terminator consists of a base sequence involved in the specific termination of RNA transcription by RNA polymerase. As the terminator, two or more of one type of terminator may be linked and used, or two or more types of terminators may be used in combination. As will be described later in the Examples, the expression system of the present embodiment can achieve a high expression level of a target protein by including two or more linked terminators.

In addition, in a case where at least one of the terminators is a terminator derived from *Arabidopsis thaliana* heat-shock protein 18.2 gene, the expression system of the present embodiment tends to be able to further increase the expression level of the target protein.

The first nucleic acid fragment may have, for example, a 5'-untranslated region (UTR) and a polyadenylation signal in addition to a promoter, a nucleic acid fragment encoding a target protein, and a terminator.

Inclusion of the 5'-UTR may further increase the expression efficiency of the target protein. Examples of the 5'-UTR include 5'-UTR of tobacco mosaic virus, 5'-UTR of *Arabidopsis thaliana* alcohol dehydrogenase gene, 5'-UTR of *Arabidopsis thaliana* elongation factor 1α-A3 gene, and 5'-UTR of rice alcohol dehydrogenase gene.

In the expression system of the present embodiment, the second nucleic acid fragment contains an expression cassette of the geminivirus-derived Rep/RepA protein. The expression cassette of the Rep/RepA protein is not particularly limited as long as the Rep/RepA protein can be expressed in host plant cells. The expression cassette of the Rep/RepA protein may have a promoter, a nucleic acid fragment encoding a Rep/RepA protein, a terminator, a 5'-UTR, a polyadenylation signal, and the like. Here, as the promoter of the Rep/RepA protein, for example, a geminivirus-derived LIR may also be used because it has promoter activity, in addition to those described above as being usable for the first nucleic acid fragment.

As used herein, the term "expression system" refers to a system capable of expressing a target protein by introducing into a plant cell a first nucleic acid fragment and a second nucleic acid fragment in combination. The expression system may be constituted of a single nucleic acid fragment or may be constituted of a combination of two or more nucleic acid fragments as long as the effects of the present invention can be obtained. Here, the nucleic acid fragment may be a vector.

That is, in the expression system of the present embodiment, the first nucleic acid fragment and the second nucleic acid fragment may be separately present as independent nucleic acid fragments, or may be linked to form a single nucleic acid fragment.

In addition, in a case where the first nucleic acid fragment and the second nucleic acid fragment are linked, the order of linkage is not particularly limited. The first nucleic acid fragment may be present on the 5' side or the second nucleic acid fragment may be present on the 5' side.

In the expression system of the present embodiment, LIR, SIR, and Rep/RepA used are those derived from geminivirus. The geminivirus is not particularly limited as long as it has a rolling circle DNA replication mechanism. Examples of the geminivirus include kidney bean yellow dwarf virus (BeYDV), tomato golden mosaic virus (TGMV), African cassava mosaic virus (ACMV), and rose leaf curl virus (RLCV), all of which belong to the genus *Mastrevirus* of the family Geminiviridae.

The base sequence of LIR derived from geminivirus is set forth in SEQ ID NO: 23. In addition, the base sequence of SIR derived from geminivirus is set forth in SEQ ID NO: 24. In addition, the base sequence of the Rep/RepA protein (open reading frames C1 and C2 encoding the Rep/RepA protein which is a replication initiation protein of BeYDV) derived from geminivirus is set forth in SEQ ID NO: 25.

The base sequence of LIR, the base sequence of SIR, and the base sequence encoding a Rep/RepA protein may have mutations with respect to the base sequences of SEQ ID NOS: 23, 24, and 25, respectively, or the base sequences of SEQ ID NOS: 23, 24, and 25 may be partially deleted, as long as they have a function with which the expression cassette of the target protein linked between LIR and SIR is replicated with high copy number by the Rep/RepA protein encoded by the above base sequence.

In a case where the base sequence of LIR, the base sequence of SIR, and the base sequence encoding a Rep/RepA protein have mutations or deletions with respect to the base sequences of SEQ ID NOS: 23, 24, and 25, respectively, each base sequence preferably has, for example, 70% or more sequence identity, more preferably 80% or more sequence identity, still more preferably 90% or more sequence identity, and particularly preferably 95% or more sequence identity, with respect to the base sequences of SEQ ID NOS: 23, 24, and 25, respectively.

Here, the sequence identity of the target base sequence with respect to the reference base sequence can be determined, for example, according to the above-mentioned formula (1).

The expression system of the present embodiment may further include a third nucleic acid fragment containing an expression cassette of a gene-silencing suppressor. Thereby, the expression level of the target protein can be further increased. Examples of the gene-silencing suppressor include a gene-silencing suppressor P19 derived from tomato bushy stunt virus, and a gene-silencing suppressor 16K derived from tobacco rattle virus.

The third nucleic acid fragment may be present separately as a nucleic acid fragment independent of the first nucleic acid fragment and the second nucleic acid fragment described above or may be linked to the first nucleic acid fragment or the second nucleic acid fragment in any order. The first nucleic acid fragment, the second nucleic acid fragment, and the third nucleic acid fragment may be linked in any order. That is, the first nucleic acid fragment, the second nucleic acid fragment, and the third nucleic acid fragment may be contained in a single vector.

The expression system of the present embodiment may be configured such that the first nucleic acid fragment, the second nucleic acid fragment, and the third nucleic acid fragment are contained in a single vector; the vector further includes RB and LB of T-DNA; and first nucleic acid fragment, the second nucleic acid fragment, and the third nucleic acid fragment are present between RB and LB of T-DNA.

T-DNA is a specific region of Ti plasmid or Ri plasmid found in a pathogenic strain of *Agrobacterium* which is a pathogenic bacterium of crown gall which is a tumor of dicotyledonous plants. Coexistence of a T-DNA-harboring *Agrobacterium* with a plant cell transfers the nucleic acid fragment present between RB and LB into a host plant cell.

Therefore, the first nucleic acid fragment, the second nucleic acid fragment, and the third nucleic acid fragment can be easily introduced into a host plant cell in such a manner that a vector in which the first nucleic acid fragment, the second nucleic acid fragment, and the third nucleic acid fragment are present between RB and LB is introduced into *Agrobacterium*, and then the *Agrobacterium* is introduced into a host plant.

The vector in which the first nucleic acid fragment, the second nucleic acid fragment, and the third nucleic acid fragment are present between RB and LB is preferably a vector that can be used in a binary vector method.

The binary vector method is a method of gene transfer into a plant using a vir helper Ti plasmid from which the native T-DNA of the Ti plasmid has been removed and a small shuttle vector having artificial T-DNA. Here, the shuttle vector is preferably one that can be maintained in both *E. coli* and *Agrobacterium*.

The vir helper Ti plasmid cannot form crown galls on plants because it does not have native T-DNA. However, the vir helper Ti plasmid has a vir region necessary for introducing T-DNA into host plant cells.

Therefore, a desired nucleic acid fragment can be easily introduced into a host plant cell by introducing T-DNA having the desired nucleic acid fragment into *Agrobacterium* having the vir helper Ti plasmid and introducing the *Agrobacterium* into the host plant.

That is, the vector in which the first nucleic acid fragment, the second nucleic acid fragment, and the third nucleic acid fragment are present between RB and LB may be a shuttle vector that has an origin of replication for *E. coli* and an origin of replication for *Agrobacterium* and can be maintained in both *E. coli* and *Agrobacterium*.

The base sequence of RB of T-DNA is set forth in SEQ ID NO: 26. In addition, the base sequence of LB of T-DNA is set forth in SEQ ID NO: 27.

The base sequences of RB and LB may have mutations with respect to the base sequences of SEQ ID NOS: 26 and 27, respectively, or the base sequences of SEQ ID NOS: 26 and 27 may be partially deleted, as long as they have a function of transferring the nucleic acid fragment present between RB and LB into the host plant cell.

In a case where the base sequences of RB and LB have mutations or deletions with respect to the base sequences of SEQ ID NOS: 26 and 27, respectively, each base sequence preferably has, for example, 70% or more sequence identity, more preferably 80% or more sequence identity, still more preferably 90% or more sequence identity, and particularly preferably 95% or more sequence identity, with respect to the base sequences of SEQ ID NOS: 26 and 27, respectively.

Here, the sequence identity of the target base sequence with respect to the reference base sequence can be determined, for example, according to the above-mentioned formula (1).

[Expression Vector]

In one embodiment, the present invention provides an expression vector including a first nucleic acid fragment containing an LIR derived from geminivirus, an SIR derived from geminivirus, and an expression cassette linked between the LIR and the SIR, in which the expression cassette includes a promoter, a multicloning site, and two or more linked terminators in this order.

The expression vector of the present embodiment can be suitably used for construction of the expression system described above. As will be described later in the Examples, the expression vector of the present embodiment can achieve a very high expression level of a target protein by introducing a gene fragment encoding the target protein at the multicloning site of the expression cassette. This is because the expression cassette contains two or more linked terminators.

In the expression vector of the present embodiment, the expression cassette preferably contains two terminators. As will be described later in the Examples, the expression level of the target protein tends to be higher in a case where the expression cassette contains two terminators than in a case where the expression cassette contains three or more terminators.

In addition, in the expression vector of the present embodiment, it is preferable that at least one of the terminators contained in the expression cassette be a terminator derived from *Arabidopsis thaliana* heat-shock protein 18.2 gene.

As will be described later in the Examples, an expression vector containing a terminator derived from *Arabidopsis thaliana* heat-shock protein 18.2 gene as the terminator tends to have a high expression level of the target protein.

In the expression vector of the present embodiment, LIR, SIR, promoter, and terminator are as described above. That is, in the expression vector of the present embodiment, the geminivirus may be a bean yellow dwarf virus (BeYDV).

As used herein, the term "multicloning site" refers to a region in which one or a plurality of base sequences recognized by restriction enzymes are arranged. That is, in the multicloning site of the expression vector of the present embodiment, the number of restriction enzyme sites may be one or plural. Since the vector of the present embodiment has a multicloning site, a nucleic acid fragment encoding a target protein can be easily cloned therein.

The expression vector of the present embodiment need not contain a nucleic acid fragment encoding a target protein, or a nucleic acid fragment encoding a target protein may be introduced therein. That is, a vector into which a nucleic acid fragment encoding a target protein has been introduced is also included in the expression vector of the present embodiment.

The vector of the present embodiment may further include a second nucleic acid fragment containing an expression cassette of a Rep/RepA protein derived from geminivirus. The Rep/RepA protein is as described above.

The vector of the present embodiment may further include a third nucleic acid fragment containing an expression cassette of a gene-silencing suppressor. The gene-silencing suppressor is as described above and may be, for example, a gene-silencing suppressor P19 derived from tomato bushy stunt virus.

The vector of the present embodiment further includes RB and LB of T-DNA, and the first nucleic acid fragment, the second nucleic acid fragment, and the third nucleic acid fragment may be present between RB and LB of T-DNA. RB and LB are as described above. In addition, it is preferable that the vector of the present embodiment be a vector which can be used for a binary vector method.

[Method for Producing Target Protein]

In one embodiment, the present invention provides a method for producing a target protein, including a step of introducing the expression system described above into a plant cell. Here, the expression system may be one in which a gene fragment encoding a target protein is introduced into the multicloning site of the vector described above. As will be described later in the Examples, according to the production method of the present embodiment, it is possible to produce a target protein with a high expression level, using plants of the genus *Nicotiana* and plants other than those belonging to the genus *Nicotiana* as hosts.

EXAMPLES

Hereinafter, the present invention will be described in more detail by way of examples, but the present invention is not limited to the following examples.

[Materials and Methods]

(Transient Expression in Lettuce)

First, an *Agrobacterium tumefaciens* GV3101 strain harboring a binary vector was cultured in a YEB medium (6 g/L of yeast extract, 5 g/L of tryptone, 5 g/L of sucrose, and 2 mM magnesium sulfate) supplemented with antibiotics (100 mg/L of kanamycin, 30 mg/L of gentamycin, and 30 mg/L of rifampin) at 28° C. for 2 days.

Subsequently, the 2-day culture was diluted 100 times with the same medium as above, MES was added to a final concentration of 10 mM to adjust the pH to 5.6, and acetosyringone was further added to a final concentration of 20 µM, followed by culturing at 28° C. for 18 to 24 hours using a rotary shaker set at 140 rpm and then scale-up.

Subsequently, after an $OD_{595}$ reached about 2.4, sucrose was added to a final concentration of 55 g/L, and acetosyringone was further added to a final concentration of 200 µM, followed by incubation at 22° C. for 1 hour.

Then, 2,4-dichlorophenoxyacetic acid was added to a final concentration of 100 µg/mL, and Tween-20 was further added to a final concentration of 0.005%, followed by vacuum infiltration.

Subsequently, commercially available red leaf lettuce was rinsed with distilled water and the water was removed with a paper towel. Subsequently, the base of the rinsed lettuce was placed on a wet paper towel. Subsequently, the lettuce was covered with plastic wrap and allowed to stand at 24° C. for 1 day. Subsequently, the lettuce was illuminated with blue LED light for more than 30 minutes prior to vacuum infiltration.

Figure 1B:
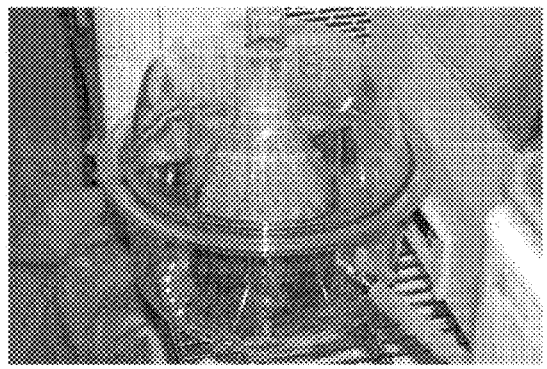
FIG. 1B is a photograph showing a state in which lettuce is immersed in the *Agrobacterium* suspension which is then set at a pressure of 736 mmHg.

Subsequently, as shown in FIG A1A, about 1.2 L of an *Agrobacterium* suspension was placed in a 2 L glass beaker inside a vacuum desiccator. Subsequently, as shown in FIG. 1B, the lettuce was immersed in the *Agrobacterium* suspension and then set at a pressure of 736 mmHg and allowed to stand for 20 minutes. Subsequently, the pressure was returned to atmospheric pressure and the lettuce was rinsed with water.

Figure 1C:
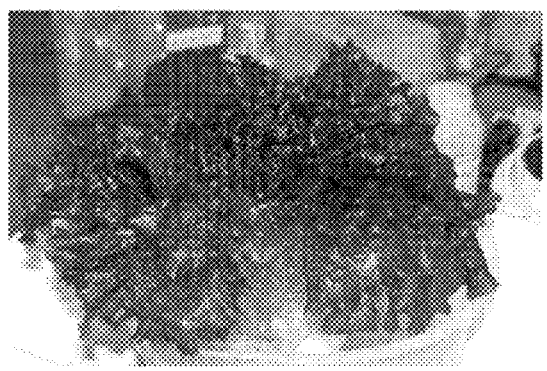
FIG. 1C is a photograph showing a state in which the agroinfiltrated lettuce is placed in a bowl.
Figure 1D:
FIG. 1D is a photograph showing a state in which the agroinfiltrated lettuce is incubated.

Subsequently, the water was removed with a paper towel. Subsequently, the base of the rinsed lettuce was covered with a wet paper towel and the lettuce was placed in a bowl as shown in FIG. 1C. Subsequently, as shown in FIG. 1D, the lettuce was partially covered with plastic wrap, leaving some holes. The lettuce was allowed to stand for 3 to 5 days at 24° C. under a 16-h light and 8-h dark photoperiod.

(Transient Expression in *Nicotiana benthamiana*, Tomato, Eggplant, Hot Pepper, Melon, Rose, and Phalaenopsis Orchid)

First, an *Agrobacterium tumefaciens* GV3101 strain harboring a binary vector was cultured in an L-broth medium supplemented with 10 mM MES (pH 5.6), 20 μM acetosyringone, 100 mg/L of kanamycin, 30 mg/L of gentamycin, and 30 mg/L of rifampin to a stationary phase at 28° C.

Subsequently, the culture was centrifuged to recover *Agrobacterium tumefaciens* which was then suspended using an infiltration buffer (10 mM magnesium chloride, 10 mM MES (pH 5.6), and 100 μM acetosyringone) so that the $OD_{600}$ was about 1. Subsequently, *Agrobacterium tumefaciens* was left in this liquid for 2 to 3 hours.

Then, the suspension of *Agrobacterium tumefaciens* was infiltrated on the reverse side of 4-week-old *Nicotiana benthamiana* leaves using a 1 mL syringe without a needle. Alternatively, in some cases, *Nicotiana benthamiana* was immersed in the *Agrobacterium* suspension which was then allowed to stand for 20 minutes under a pressure of 736 mmHg, followed by infiltration by returning the pressure to atmospheric pressure. In addition, the same suspension was similarly infiltrated into 4-week-old tomato leaves, 4-week-old eggplant leaves, 4-week-old hot pepper leaves, 3-week-old melon leaves, commercially available rose petals, and commercially available phalaenopsis orchid petals. In addition, the same suspension was infiltrated into tomato fruits using a 1 mL syringe equipped with a needle.

(Construction of Vector)

<<Construction of pBYR2fp-EGFP Vector>>

Figure 2A:
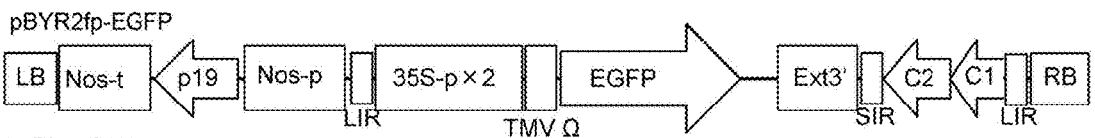
FIG. 2A is a schematic diagram of a T-DNA region of a pBYR2fp-EGFP vector.

FIG. 2A is a schematic diagram of the T-DNA region of the pBYR2fp-EGFP vector (by courtesy of Dr. Mason, Arizona State University, USA). The pBYR2fp vector, a known vector, has a replication system derived from bean yellow dwarf virus (BeYDV). In addition, the pBYR2fp vector has an expression cassette of the gene-silencing suppressor P19 derived from tomato bushy stunt virus.

First, an enhanced green fluorescence protein (EGFP) gene fragment was subjected to PCR amplification using a primer (pBYR2fp-EGFP-F, SEQ ID NO: 1) and a primer (EGFP-pBYR2fp-R, SEQ ID NO: 2). Subsequently, the resulting PCR product was cloned into the pBYR2fp vector digested with an restriction enzyme XbaI to construct a pBYR2fp-EGFP vector.

<<Construction of pBYR2HS-EGFP Vector>>

Figure 2B:
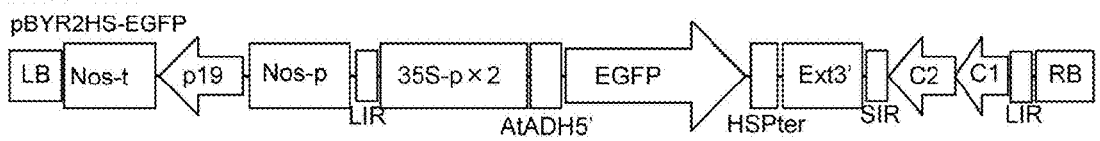
FIG. 2B is a schematic diagram of a T-DNA region of a pBYR2HS-EGFP vector.

FIG. 2B is a schematic diagram of the T-DNA region of the pBYR2HS-EGFP vector. An EGFP gene fragment having an alcohol dehydrogenase gene 5'-UTR and an *Arabidopsis thaliana* heat-shock protein 18.2 gene terminator was introduced into the pBYR2fp vector.

Specifically, first, the EGFP gene fragment was subjected to PCR amplification using a primer (pRI201-EGFP-F, SEQ ID NO: 3) and a primer (EGFP-pRI201-R, SEQ ID NO: 4).

Subsequently, the resulting PCR product was cloned into pRI201-AN (available from Takara Bio Inc.) digested with restriction enzymes NdeI and SalI to construct a pRI201-EGFP vector.

Subsequently, using the pRI201-EGFP vector as a template, a primer (pBYR2fp-AtADH-F, SEQ ID NO: 5) and a primer (pBYR2fp-HSPter-R, SEQ ID NO: 6), the EGFP gene fragment having an alcohol dehydrogenase gene 5'-UTR and an *Arabidopsis thaliana* heat-shock protein 18.2 gene terminator was subjected to PCR amplification.

Subsequently, the resulting PCR product was cloned into the pBYR2fp vector digested with restriction enzymes XhoI and XbaI to construct a pBYR2HS-EGFP vector. The full-length base sequence of the pBYR2HS-EGFP vector is set forth in SEQ ID NO: 28.

<<Construction of pBYR2EE-EGFP Vector>>

Figure 2C:
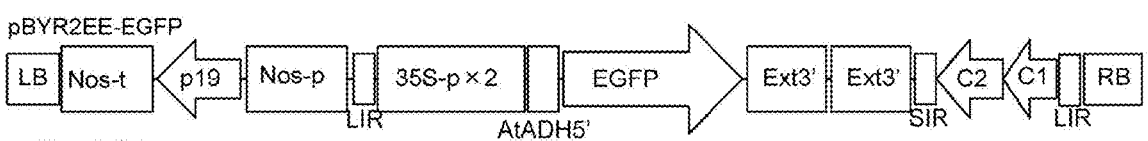
FIG. 2C is a schematic diagram of a T-DNA region of a pBYR2EE-EGFP vector.

FIG. 2C is a schematic diagram of the T-DNA region of the pBYR2EE-EGFP vector. The tobacco extensin gene terminator was subjected to PCR amplification using the pBYR2HS-EGFP vector as a template and using a primer (pBYR2EE-Ext3-F, SEQ ID NO: 7) and a primer (pBYR2EE-Ext3-R, SEQ ID NO: 8). The resulting PCR product was cloned into the pBYR2HS-EGFP vector digested with restriction enzymes SalI and XbaI to construct a pBYR2EE-EGFP vector. The terminator of the pBYR2EE-EGFP vector was one in which two tobacco extensin gene terminators were linked to each other.

<<Construction of pBYR2HH-EGFP Vector>>

Figure 2D:
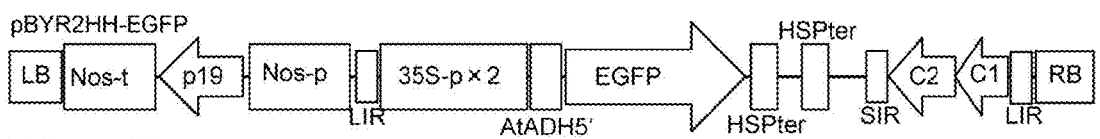
FIG. 2D is a schematic diagram of a T-DNA region of a pBYR2HH-EGFP vector.

FIG. 2D is a schematic diagram of the T-DNA region of the pBYR2HH-EGFP vector. The *Arabidopsis thaliana* heat-shock protein 18.2 gene terminator was subjected to PCR amplification using the pBYR2HS-EGFP vector as a template and using a primer (pBYR2H-HSPter-F, SEQ ID NO: 9) and a primer (pBYR2H-HSPter-R, SEQ ID NO: 10). The PCR product was cloned into the pBYR2H-EGFP vector digested with a restriction enzyme XbaI to construct a pBYR2HH-EGFP vector. The terminator of the pBYR2HH-EGFP vector was one in which two *Arabidopsis thaliana* heat-shock protein 18.2 gene terminators were linked to each other.

<<Construction of pBYR2H-EGFP Vector>>

Figure 2E:
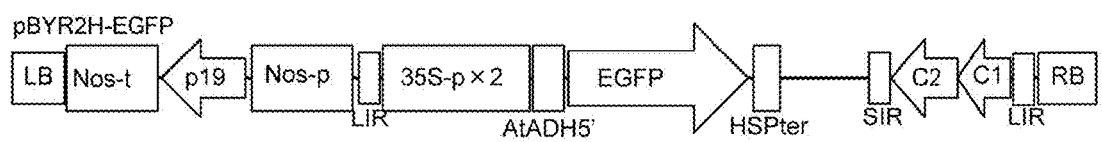
FIG. 2E is a schematic diagram of a T-DNA region of a pBYR2H-EGFP vector.

FIG. 2E is a schematic diagram of the T-DNA region of the pBYR2H-EGFP vector. In order to remove the tobacco extensin gene terminator from pBYR2HS-EGFP, it was digested with restriction enzymes XmaI and ClaI. SIR-C2 was subjected to PCR amplification using the pBYR2HS-EGFP vector as a template and using a primer (HSPter-SIR-F, SEQ ID NO: 11) and a primer (C1-ClaI-C2-R, SEQ ID NO: 12). The PCR product was cloned into the foregoing XmaI/ClaI-digested pBYR2HS-EGFP to construct a pBYR2H-EGFP vector. The terminator of the pBYR2H-EGFP vector was one which has one *Arabidopsis thaliana* heat-shock protein 18.2 gene terminator.

<<Construction of pBYR2TN-EGFP Vector>>

Figure 2F:
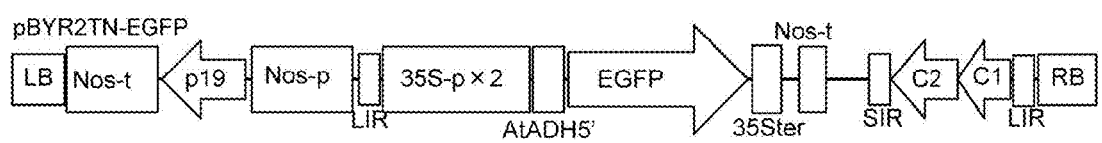
FIG. 2F is a schematic diagram of a T-DNA region of a pBYR2TN-EGFP vector.

FIG. 2F is a schematic diagram of the T-DNA region of the pBYR2TN-EGFP vector. The cauliflower mosaic virus (CaMV) 35S terminator was subjected to PCR amplification using pCambia1391Z (available from Marker Gene Technologies, Inc.) as a template and using a primer (pBYR2T-35Ster-F, SEQ ID NO: 13) and a primer (35Ster-NOSter-R, SEQ ID NO: 14). The NOS terminator was subjected to PCR amplification using pRI201-AN (available from Takara Bio Inc.) as a template and using a primer (35Ster-NOSter-F, SEQ ID NO: 15) and a primer (pBYR2TN-NOSter-R, SEQ ID NO: 16). The PCR products were cloned into the pBYR2H-EGFP vector digested with restriction enzymes SalI and XbaI to construct a pBYR2TN-EGFP vector. The terminator of the pBYR2TN-EGFP vector was one in which one cauliflower mosaic virus (CaMV) 35S terminator and one NOS terminator were linked to each other.

<<Construction of pBYR2T-EGFP Vector>>

Figure 2G:
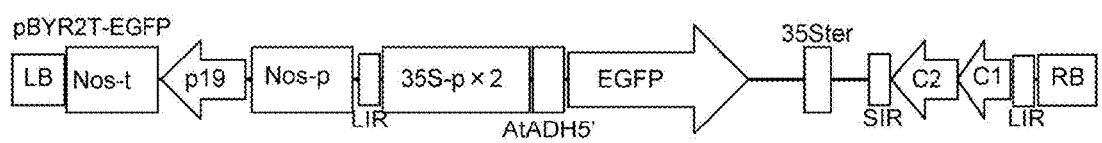
FIG. 2G is a schematic diagram of a T-DNA region of a pBYR2T-EGFP vector.

FIG. 2G is a schematic diagram of the T-DNA region of the pBYR2T-EGFP vector. The cauliflower mosaic virus (CaMV) 35S terminator was subjected to PCR amplification using pCambia1391Z as a template and using a primer (pBYR2T-35Ster-F, SEQ ID NO: 13) and a primer (pBYR2HS-35Ster-R, SEQ ID NO: 17). The PCR product was cloned into the pBYR2H-EGFP vector digested with restriction enzymes SalI and XbaI to construct a pBYR2T-EGFP vector. The terminator of the pBYR2T-EGFP vector was one which has one cauliflower mosaic virus (CaMV) 35S terminator.

<<Construction of pBYR2HT-EGFP Vector>>

Figure 2H:
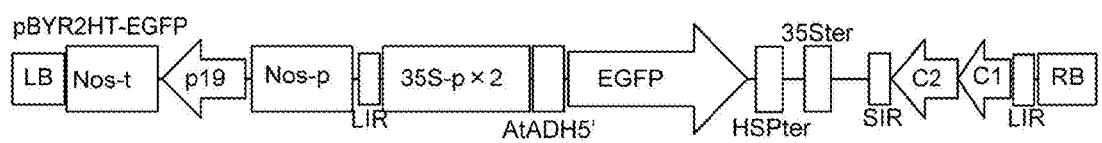
FIG. 2H is a schematic diagram of a T-DNA region of a pBYR2HT-EGFP vector.

FIG. 2H is a schematic diagram of the T-DNA region of the pBYR2HT-EGFP vector. The cauliflower mosaic virus (CaMV) 35S terminator was subjected to PCR amplification using pCambia1391Z as a template and using a primer (pBYR2HS-35Ster-F, SEQ ID NO: 18) and a primer (pBYR2HS-35Ster-R, SEQ ID NO: 17). The PCR product was cloned into the pBYR2H-EGFP vector digested with a restriction enzyme XbaI to construct a pBYR2HT-EGFP vector. The terminator of the pBYR2HT-EGFP vector was one in which one Arabidopsis thaliana heat-shock protein 18.2 gene terminator and one cauliflower mosaic virus (CaMV) 35S terminator were linked to each other.

<<Construction of pBYR2HTS-EGFP Vector>>

Figure 2I:
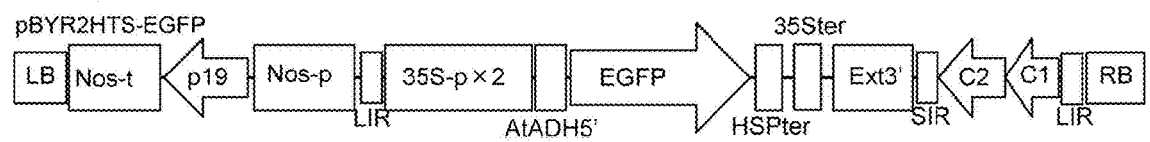
FIG. 2I is a schematic diagram of a T-DNA region of a pBYR2HTS-EGFP vector.

FIG. 2I is a schematic diagram of the T-DNA region of the pBYR2HTS-EGFP vector. The cauliflower mosaic virus (CaMV) 35S terminator was subjected to PCR amplification using pCambia1391Z as a template and using a primer (pBYR2HS-35Ster-F, SEQ ID NO: 18) and a primer (pBYR2HS-35Ster-R, SEQ ID NO: 17). The PCR product was cloned into pBYR2HS-EGFP vector digested with a restriction enzyme XbaI to construct a pBYR2HTS-EGFP vector. The terminator of the pBYR2HTS-EGFP vector was one in which one Arabidopsis thaliana heat-shock protein 18.2 gene terminator, one cauliflower mosaic virus (CaMV) 35S terminator, and one tobacco extensin gene terminator were linked to one another.

In FIGS. 2A to 2I, "35S-px2" refers to a cauliflower mosaic virus (CaMV) 35S promoter having two enhancement elements; "TMVΩ" refers to a tobacco mosaic virus 5'-UTR; "AtADH5" refers to an Arabidopsis thaliana alcohol dehydrogenase gene 5'-UTR; "EGFP" refers to an enhanced green fluorescence protein; "Ext3" refers to a tobacco extensin gene terminator; "HSPter" refers to an Arabidopsis thaliana heat-shock protein 18.2 gene terminator; "35Ster" refers to a cauliflower mosaic virus (CaMV) 35S terminator; "Nos-t" refers to a NOS terminator; "LIR" refers to a long intergenic region of the bean yellow dwarf virus (BeYDV) genome; "SIR" refers to a short intergenic region of the BeYDV genome; "C1" and "C2" refer to open reading frames C1 and C2 encoding Rep/RepA protein which is replication initiation protein of BeYDV; "LB" and "RB" refer to a left border sequence and a right border sequence of T-DNA, respectively; "Nos-p" refers to a NOS promoter; and "p19" refers to a gene encoding a gene-silencing suppressor P19 derived from tomato bushy stunt virus.

Experimental Example 1

(Comparison 1 of Expression Levels of EGFP with pBYR2HS-EGFP Vector and pBYR2fp-EGFP Vector)

The pBYR2HS-EGFP vector was a vector having two terminators in which the TMVΩ of the pBYR2fp-EGFP vector is replaced by the Arabidopsis thaliana alcohol dehydrogenase gene 5'-UTR and the Arabidopsis thaliana heat-shock protein 18.2 gene terminator is inserted.

An outline of the pBYR2HS-EGFP vector and the pBYR2fp-EGFP vector is shown in Table 1 below. In Table 1, "HSPter" refers to an Arabidopsis thaliana heat-shock protein 18.2 gene terminator, and "Ext3" refers to a tobacco extensin gene terminator.

TABLE 1

| Vector | Number of terminators | Type of terminator |
| --- | --- | --- |
| pBYR2HS-EGFP | 2 | HSPter, Ext3' |
| pBYR2fp-EGFP | 1 | Ext3' |

The pBYR2HS-EGFP vector and the pBYR2fp-EGFP vector were respectively introduced into Agrobacterium tumefaciens GV3101 strains which were then introduced into Nicotiana benthamiana leaves, lettuce leaves, eggplant leaves, tomato fruits, tomato leaves, hot pepper leaves, melon leaves, rose petals, and phalaenopsis orchid petals, respectively.

After introduction of the vectors, each plant was incubated for 3 days to transiently express EGFP. Subsequently, each plant was irradiated with a blue LED, and the fluorescence of EGFP was observed using an ultraviolet absorbing filter (Model "SC-52", available from Fujifilm Corporation).

FIGS. 3A to 3I are photographs showing the results of observing the fluorescence of expressed EGFP. In FIGS. 3A to 3I, the scale bars indicate 1 cm length. FIG. 3A shows the results of Nicotiana benthamiana leaves, FIG. 3B shows the results of lettuce leaves, FIG. 3C shows the results of eggplant leaves, FIG. 3D shows the results of tomato fruits, FIG. 3E shows the results of tomato leaves, FIG. 3F shows the results of hot pepper leaves, FIG. 3G shows the results of melon leaves, FIG. 3H shows the results of rose petals, and FIG. 3I shows the results of phalaenopsis orchid petals. In any of the photographs, the left side shows the results of introduction of the pBYR2HS-EGFP vector, and the right side shows the results of introduction of the pBYR2fp-EGFP vector.

As a result, with the exception of rose, it was found that the introduction of the pBYR2HS-EGFP vector increased the expression level of EGFP more than the introduction of the pBYR2fp-EGFP vector. In the rose, no fluorescence of EGFP was observed in a case where any of the vectors was introduced.

Moreover, in particular, in tomato fruits and tomato leaves, the fluorescence of EGFP was observed only in a case where the pBYR2HS-EGFP vector was introduced, and the fluorescence of EGFP was hardly observed in a case where the pBYR2fp-EGFP vector was introduced.

From the results, it was demonstrated that the expression level of EGFP was significantly higher in the pBYR2HS- EGFP vector having two terminators of tobacco extensin gene terminator and *Arabidopsis thaliana* heat-shock protein 18.2 gene-derived terminator than in the pBYR2fp-EGFP vector having one tobacco extensin gene terminator.

Experimental Example 2

(Comparison 2 of Expression Levels of EGFP with pBYR2HS-EGFP Vector and pBYR2fp-EGFP Vector)

The pBYR2HS-EGFP vector and the pBYR2fp-EGFP vector were respectively introduced into *Agrobacterium tumefaciens* GV3101 strains which were then introduced into *Nicotiana benthamiana* leaves, lettuce leaves, eggplant leaves, tomato leaves, hot pepper leaves, and rose petals, respectively, by means of agroinfiltration. Subsequently, each plant was incubated for 3 days to transiently express EGFP.

Subsequently, total soluble proteins were prepared from 0.2 mg fresh weight (FW) of *Nicotiana benthamiana* leaves and 1 mg fresh weight of each of lettuce leaves, eggplant leaves, tomato leaves, hot pepper leaves, and rose petals, into each of which the vector has been introduced.

Subsequently, the prepared proteins were subjected to SDS-polyacrylamide gel electrophoresis (SDS-PAGE), and total soluble proteins were detected by Coomassie Brilliant Blue (CBB) staining.

In addition, the SDS-PAGE gels were transferred to a PVDF membrane, and the EGFP protein was detected by immunoblot analysis using an anti-GFP antibody.

Figure 4A:
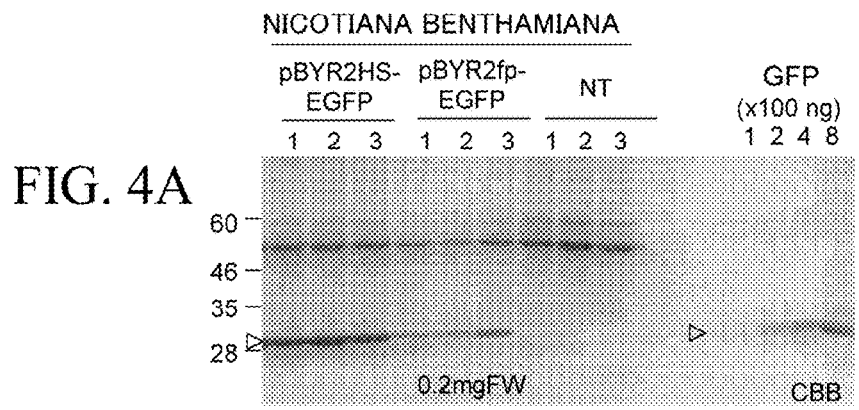
FIG. 4A is a photograph showing the results of CBB staining of SDS-PAGE gels of total soluble protein prepared from *Nicotiana benthamiana* leaves in Experimental Example 2.
Figure 4B:
FIG. 4B is a photograph showing the results of transferring the gels of FIG. 4A to a PVDF membrane and carrying out immunoblot analysis using an anti-GFP antibody.
Figure 4C:
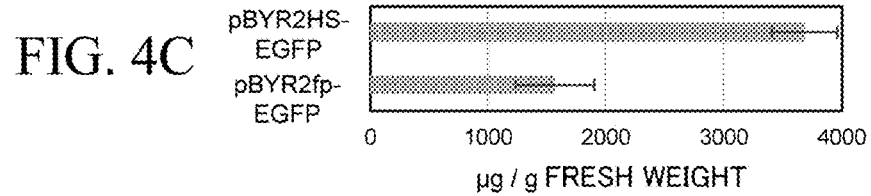
FIG. 4C is a graph in which the expression level of EGFP in FIG. 4A is quantified.

FIG. 4A is a photograph showing the results of CBB staining of SDS-PAGE gels of total soluble protein prepared from *Nicotiana benthamiana* leaves. In FIG. 4A, the arrowhead indicates an EGFP protein. In addition, "NT" refers to a total soluble protein prepared from the *Nicotiana benthamiana* leaves into which no vector has been introduced. In addition, "GFP" refers to a commercially available purified GFP protein (available from Vector Laboratories, Inc.). FIG. 4B is a photograph showing the results of transferring the gels of FIG. 4A to a PVDF membrane and carrying out immunoblot analysis using an anti-GFP antibody. FIG. 4C is a graph in which the expression level of EGFP in FIG. 4A is quantified. The numerical values in the graph of FIG. 4C are shown as mean value±standard deviation.

Figure 5A:
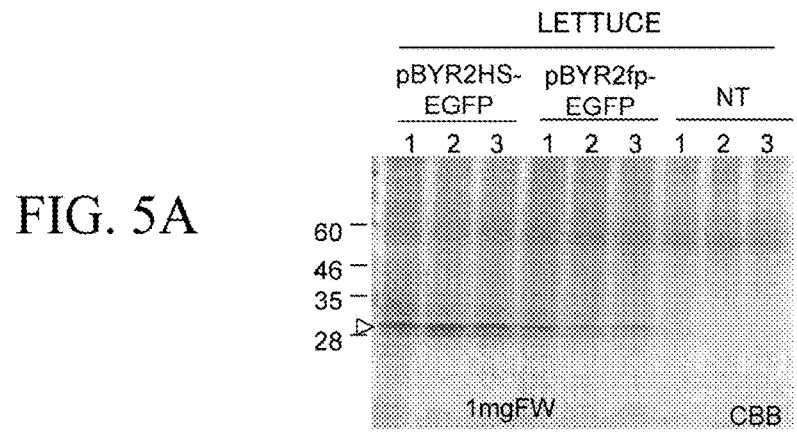
FIG. 5A is a photograph showing the results of CBB staining of SDS-PAGE gels of total soluble protein prepared from lettuce leaves in Experimental Example 2.
Figure 5B:
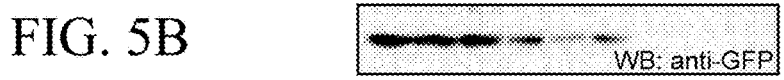
FIG. 5B is a photograph showing the results of transferring the gels of FIG. 5A to a PVDF membrane and carrying out immunoblot analysis using an anti-GFP antibody.
Figure 5C:
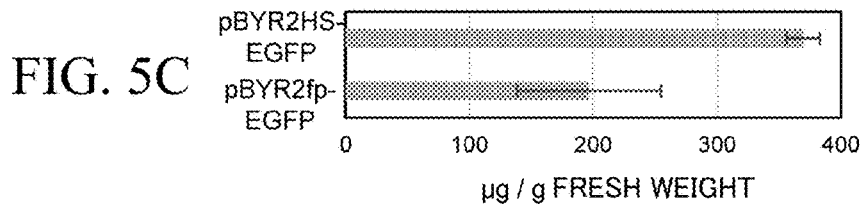
FIG. 5C is a graph in which the expression level of EGFP in FIG. 5A is quantified.

FIG. 5A is a photograph showing the results of CBB staining of SDS-PAGE gels of total soluble protein prepared from lettuce leaves. In FIG. 5A, the arrowhead indicates an EGFP protein. In addition, "NT" refers to a total soluble protein prepared from the lettuce leaves into which no vector has been introduced. FIG. 5B is a photograph showing the results of transferring the gels of FIG. 5A to a PVDF membrane and carrying out immunoblot analysis using an anti-GFP antibody. FIG. 5C is a graph in which the expression level of EGFP in FIG. 5A is quantified. The numerical values in the graph of FIG. 5C are shown as mean value±standard deviation.

Figure 6A:
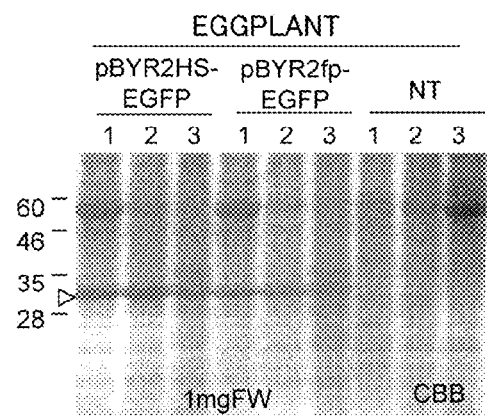
FIG. 6A is a photograph showing the results of CBB staining of SDS-PAGE gels of total soluble protein prepared from eggplant leaves in Experimental Example 2.
Figure 6B:
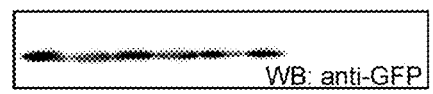
FIG. 6B is a photograph showing the results of transferring the gels of FIG. 6A to a PVDF membrane and carrying out immunoblot analysis using an anti-GFP antibody.
Figure 6C:
FIG. 6C is a graph in which the expression level of EGFP in FIG. 6A is quantified.

FIG. 6A is a photograph showing the results of CBB staining of SDS-PAGE gels of total soluble protein prepared from eggplant leaves. In FIG. 6A, the arrowhead indicates an EGFP protein. In addition, "NT" refers to a total soluble protein prepared from the eggplant leaves into which no vector has been introduced. FIG. 6B is a photograph showing the results of transferring the gels of FIG. 6A to a PVDF membrane and carrying out immunoblot analysis using an anti-GFP antibody. FIG. 6C is a graph in which the expression level of EGFP in FIG. 6A is quantified. The numerical values in the graph of FIG. 6C are shown as mean value±standard deviation.

Figure 7A:
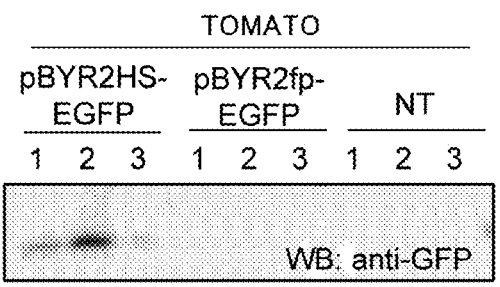
FIG. 7A is a photograph showing the results of subjecting total soluble protein prepared from tomato leaves to SDS-PAGE, transferring the SDS-PAGE gels to a PVDF membrane, and carrying out immunoblot analysis using an anti-GFP antibody in Experimental Example 2.
Figure 7B:
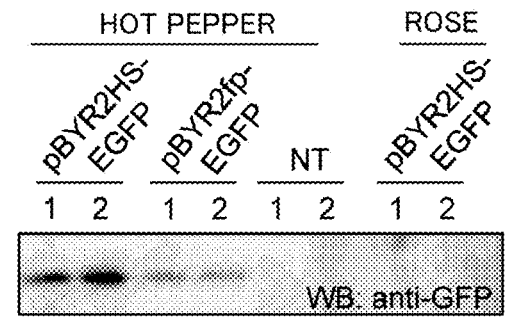
FIG. 7B is a photograph showing the results of subjecting total soluble proteins prepared from hot pepper leaves and rose petals to SDS-PAGE, transferring the SDS-PAGE gels to a PVDF membrane, and carrying out immunoblot analysis using an anti-GFP antibody.
Figure 8A:
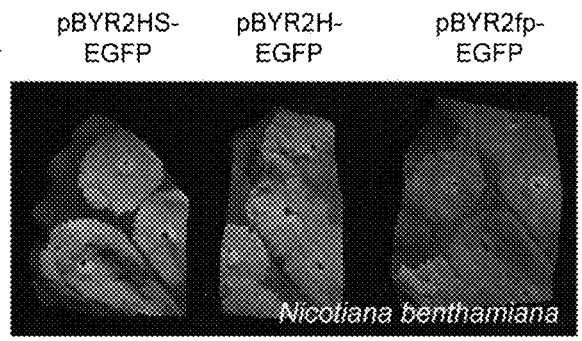
FIGS. 8A to 8E are photographs showing the results of observation of fluorescence of expressed EGFP in Experimental Example 3.
Figure 8B:
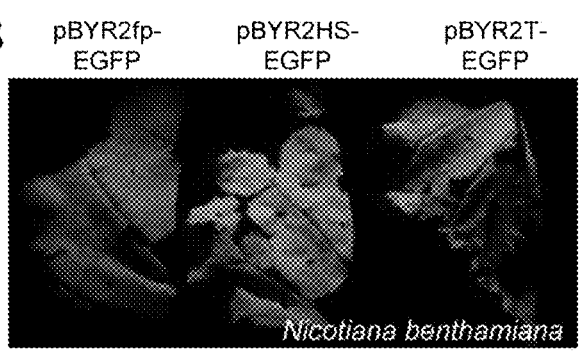
Figure 8C:
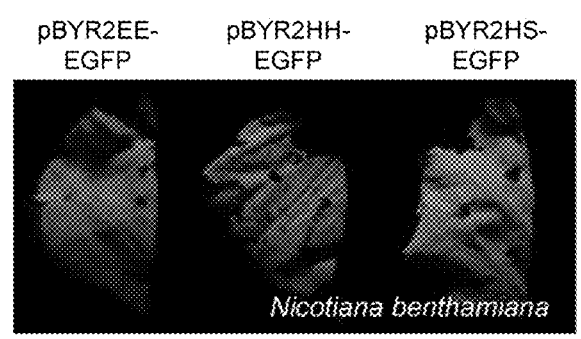
Figure 8D:
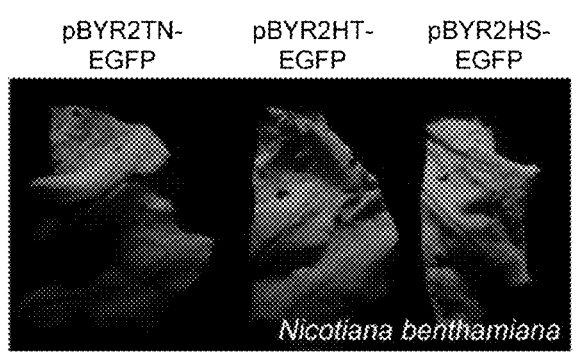
Figure 8E:
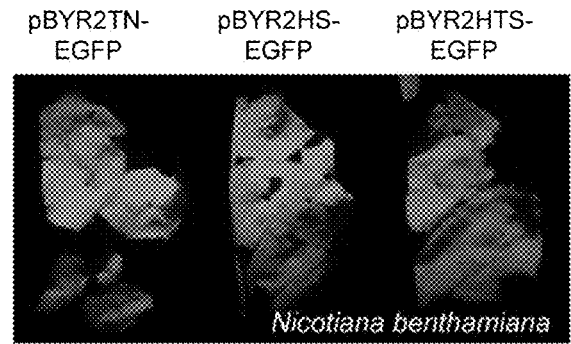

FIG. 7A is a photograph showing the results of subjecting total soluble protein prepared from tomato leaves to SDS-PAGE, transferring the SDS-PAGE gels to a PVDF membrane, and carrying out immunoblot analysis using an anti-GFP antibody. In FIG. 7A, "NT" refers to a total soluble protein prepared from the tomato leaves into which no vector has been introduced. FIG. 7B is a photograph showing the results of subjecting total soluble proteins prepared from hot pepper leaves and rose petals to SDS-PAGE, transferring the SDS-PAGE gels to a PVDF membrane, and carrying out immunoblot analysis using an anti-GFP antibody. In FIG. 7B, "NT" refers to a total soluble protein prepared from the hot pepper leaves into which no vector has been introduced.

As a result, it was demonstrated that the plants agroinfiltrated with the pBYR2HS-EGFP vector showed a significant increase in the expression level of EGFP over the plants agroinfiltrated with the pBYR2fp-EGFP vector.

Specifically, as a result of quantifying the expression level of EGFP, it was demonstrated that 3.7 mg of EGFP was expressed in 1 g fresh weight in the *Nicotiana benthamiana* into which the pBYR2HS-EGFP vector was agroinfiltrated. On the other hand, it was demonstrated that 1.5 mg of EGFP was expressed in 1 g fresh weight in the *Nicotiana benthamiana* into which the pBYR2fp-EGFP vector was agroinfiltrated.

Similarly, it was demonstrated that 0.37 mg of EGFP was expressed in 1 g fresh weight in the lettuce into which the pBYR2HS-EGFP vector was agroinfiltrated. On the other hand, it was demonstrated that 0.20 mg of EGFP was expressed in 1 g fresh weight in the lettuce into which the pBYR2fp-EGFP vector was agroinfiltrated.

In addition, it was demonstrated that 0.46 mg of EGFP was expressed in 1 g fresh weight in the eggplant into which the pBYR2HS-EGFP vector was agroinfiltrated. On the other hand, it was demonstrated that 0.42 mg of EGFP was expressed in 1 g fresh weight in the eggplant into which the pBYR2fp-EGFP vector was agroinfiltrated.

No clear EGFP bands were observed in CBB staining after SDS-PAGE for tomato leaves, hot pepper leaves, and rose petals. Therefore, only immunoblot analysis was carried out on these samples.

As a result, a significant increase in the expression level of EGFP was observed in the tomato leaves and hot pepper leaves into which the pBYR2HS-EGFP vector was agroinfiltrated, as compared with the case where the pBYR2fp-EGFP vector was agroinfiltrated.

In rose petals, the expression of EGFP was not detected even in a case where the pBYR2HS-EGFP vector was agroinfiltrated, followed by immunoblot analysis.

From the above results, it was demonstrated that the expression level of EGFP was significantly higher in the pBYR2HS-EGFP vector having two terminators of tobacco extensin gene terminator and *Arabidopsis thaliana* heat-shock protein 18.2 gene-derived terminator than in the pBYR2fp-EGFP vector having one tobacco extensin gene terminator. In addition, it was demonstrated that this expression system works not only in tobacco but also in multiple species of plants other than those belonging to the genus *Nicotiana*.

Experimental Example 3

(Comparison 1 of Expression Levels of EGFP with Vectors having Various Terminators)

pBYR2fp-EGFP vector, pBYR2H-EGFP vector, and pBYR2T-EGFP vector, each having only one terminator;

pBYR2HS-EGFP vector, pBYR2EE-EGFP vector, pBYR2HH-EGFP vector, pBYR2TN-EGFP vector, and pBYR2HT-EGFP vector, each having two terminators; and pBYR2HTS-EGFP vector having three terminators were respectively introduced into *Agrobacterium tumefaciens* GV3101 strains which were then respectively introduced into *Nicotiana benthamiana* leaves.

An outline of each vector is shown in Table 2 below. In Table 2, "Ext3'" refers to a tobacco extensin gene terminator; "HSPter" refers to an *Arabidopsis thaliana* heat-shock protein 18.2 gene terminator; "35Ster" refers to a cauliflower mosaic virus (CaMV) 35S terminator; and "Nos-t" refers to a NOS terminator.

TABLE 2

| Vector | Number of terminators | Type of terminator |
|---|---|---|
| pBYR2fp-EGFP | 1 | Ext3' |
| pBYR2H-EGFP | 1 | HSPter |
| pBYR2T-EGFP | 1 | 35STer |
| pBYR2HS-EGFP | 2 | HSPter, Ext3' |
| pBYR2EE-EGFP | 2 | Ext3', Ext3' |
| pBYR2HH-EGFP | 2 | HSPter, HSPter |
| pBYR2TN-EGFP | 2 | 35Ster, Nos-t |
| pBYR2HT-EGFP | 2 | HSPter, 35Ster |
| pBYR2HTS-EGFP | 3 | HSPter, 35Ster, Ext3' |

After introduction of the vectors, each plant was incubated for 3 days to transiently express EGFP. Subsequently, each plant was irradiated with excitation light, and the fluorescence of EGFP was observed using an ultraviolet absorbing filter (Model "SC-52", available from Fujifilm Corporation).

FIGS. 8A to 8E are photographs showing the results of observing the fluorescence of expressed EGFP. The vectors introduced are shown at the top of FIGS. 8A to 8E.

As a result, the expression level of EGFP tended to be higher in pBYR2HS-EGFP vector, pBYR2EE-EGFP vector, pBYR2HH-EGFP vector, pBYR2TN-EGFP vector, pBYR2HT-EGFP vector, and pBYR2HTS-EGFP vector, each having two or more terminators, than in pBYR2fp-EGFP vector, pBYR2H-EGFP vector, and pBYR2T-EGFP vector, each having only one terminator.

Experimental Example 4

(Comparison 2 of Expression Levels of EGFP with Vectors having Various Terminators)

pBYR2fp-EGFP vector and pBYR2H-EGFP vector each having only one terminator, and pBYR2HS-EGFP vector having two terminators were respectively introduced into *Agrobacterium tumefaciens* GV3101 strains which were then respectively introduced into *Nicotiana benthamiana* leaves by means of agroinfiltration. Subsequently, each plant was incubated for 3 days to transiently express EGFP. Subsequently, total soluble proteins were prepared from the *Nicotiana benthamiana* leaves into which the vector had been introduced.

Subsequently, the prepared protein corresponding to 0.2 mg fresh weight (FW) was subjected to SDS-polyacrylamide gel electrophoresis (SDS-PAGE) and total soluble protein was detected by Coomassie Brilliant Blue (CBB) staining.

Figure 9A:
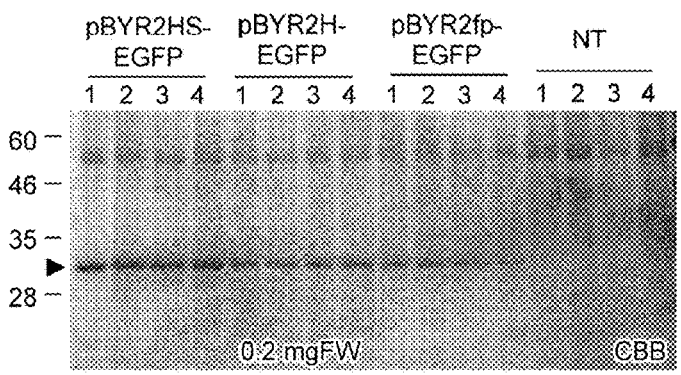
FIG. 9A is a photograph showing the results of CBB staining of SDS-PAGE gels of total soluble protein prepared from *Nicotiana benthamiana* leaves in Experimental Example 4.
Figure 9B:
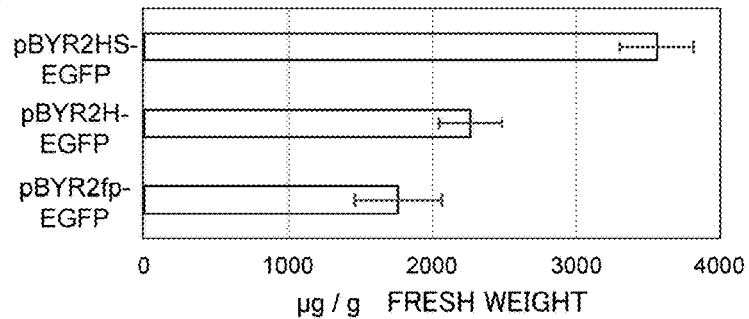
FIG. 9B is a graph in which the expression level of EGFP in FIG. 9A is quantified.

FIG. 9A is a photograph showing the results of CBB staining of SDS-PAGE gels of total soluble protein prepared from *Nicotiana benthamiana* leaves. In FIG. 9A, the arrowhead indicates an EGFP protein. In addition, "NT" refers to a total soluble protein prepared from the *Nicotiana benthamiana* leaves into which no vector has been introduced. FIG. 9B is a graph in which the expression level of EGFP in FIG. 9A is quantified. The numerical values in the graph of FIG. 9B are shown as mean value±standard deviation.

As a result, it was demonstrated that the expression level of EGFP was significantly higher in the pBYR2HS-EGFP vector having two terminators than in the pBYR2fp-EGFP vector and the pBYR2H-EGFP vector, each having only one terminator. In addition, it was demonstrated that the expression level of EGFP reached 3.7 mg in 1 g fresh weight in *Nicotiana benthamiana* into which the pBYR2HS-EGFP vector was agroinfiltrated.

Experimental Example 5

(Comparison 3 of Expression Levels of EGFP with Vectors having Various Terminators)

pBYR2HS-EGFP vector, pBYR2HH-EGFP vector, pBYR2EE-EGFP vector, pBYR2TN-EGFP vector, and pBYR2HT-EGFP vector, each having two terminators, and pBYR2HTS-EGFP vector having three terminators were respectively introduced into *Agrobacterium tumefaciens* GV3101 strains which were then respectively introduced into *Nicotiana benthamiana* leaves by means of agroinfiltration. Subsequently, each plant was incubated for 3 days to transiently express EGFP. Subsequently, total soluble proteins were prepared from the *Nicotiana benthamiana* leaves into which the vector had been introduced.

Subsequently, the prepared protein corresponding to 0.2 mg fresh weight (FW) was subjected to SDS-polyacrylamide gel electrophoresis (SDS-PAGE) and total soluble protein was detected by Coomassie Brilliant Blue (CBB) staining.

Figure 10A:
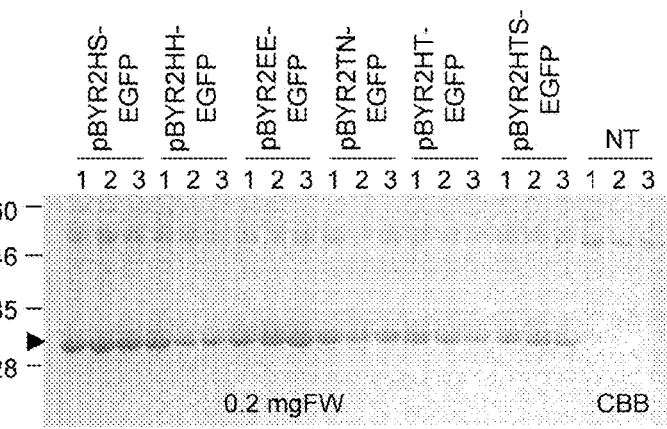
FIG. 10A is a photograph showing the results of CBB staining of SDS-PAGE gels of total soluble protein prepared from *Nicotiana benthamiana* leaves in Experimental Example 5.
Figure 10B:
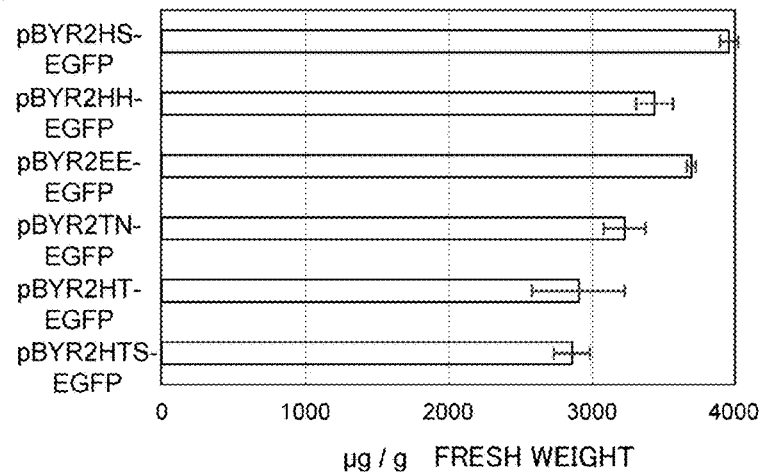
FIG. 10B is a graph in which the expression level of EGFP in FIG. 10A is quantified.

FIG. 10A is a photograph showing the results of CBB staining of SDS-PAGE gels of total soluble protein prepared from *Nicotiana benthamiana* leaves. In FIG. 9A, the arrowhead indicates an EGFP protein. In addition, "NT" refers to a total soluble protein prepared from the *Nicotiana benthamiana* leaves into which no vector has been introduced. FIG. 10B is a graph in which the expression level of EGFP in FIG. 10A is quantified. The numerical values in the graph of FIG. 10B are shown as mean value±standard deviation.

In addition, an outline of each vector used in this experimental example and the expression level of EGFP are shown in Table 3 below. In Table 3, "Ext3'" refers to a tobacco extensin gene terminator; "HSPter" refers to an *Arabidopsis thaliana* heat-shock protein 18.2 gene terminator; "35Ster" refers to a cauliflower mosaic virus (CaMV) 35S terminator; and "Nos-t" refers to a NOS terminator. In addition, the expression level of EGFP is shown as mean value±standard deviation.

TABLE 3

| Vector | Number of terminators | Type of terminator | Expression level of EGFP (mg/g fresh weight) |
|---|---|---|---|
| pBYR2HS-EGFP | 2 | HSPter, Ext3' | 3.9 + 0.1 |
| pBYR2HH-EGFP | 2 | HSPter, HSPter | 3.4 + 0.1 |
| pBYR2EE-EGFP | 2 | Ext3', Ext3' | 3.7 + 0.1 |
| pBYR2TN-EGFP | 2 | 35Ster, Nos-t | 3.2 + 0.1 |
| pBYR2HT-EGFP | 2 | HSPter, 35Ster | 2.9 + 0.3 |
| pBYR2HTS-EGFP | 3 | HSPter, 35Ster, Ext3' | 2.9 + 0.1 |

As a result, high expression of EGFP was observed in any of the vectors. Specifically, expression of EGFP of about 3 mg or more per 1 g fresh weight of a plant was observed in any of the vectors. In addition, the vector having two terminators tended to exhibit a higher expression level of EGFP than the vector having three terminators. In addition, the vector containing an *Arabidopsis thaliana* heat-shock protein 18.2 gene terminator as the terminator tended to exhibit a particularly high expression level of EGFP. In particular, in the pBYR2HS-EGFP vector, expression of EGFP of about 4 mg was observed per 1 g fresh weight of a plant.

Experimental Example 6

(Comparison of Expression Levels of Proteins with pBYR2HS-EGFP Vector and MagnICON System)

As described above, the magnICON system is a currently commercially available expression system, and is known to be able to express a target protein of about 3 mg or more per 1 g fresh weight of a plant. Therefore, the expression levels of proteins with the pBYR2HS-EGFP vector and the magnICON system described above were compared.

Figure 11:
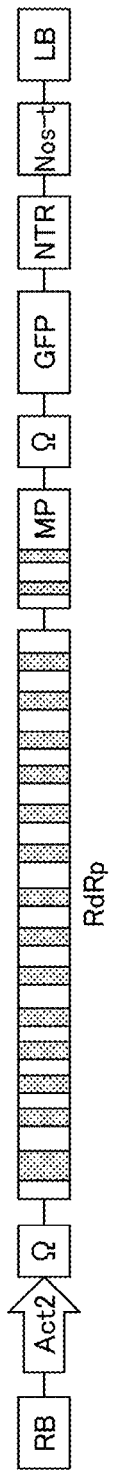
FIG. 11 is a schematic diagram showing a structure of a GFP_pICH18711 vector.

FIG. 11 is a schematic diagram showing the structure of a GFP_pICH18711 vector (by courtesy of Dr. Klimyuk at Icon Genetics GmbH), which is an expression vector using the magnICON system.

In FIG. 11, "RB" and "LB" refer to a right border sequence and a left border sequence of T-DNA, respectively; "Act2" refers to an Act2 promoter derived from *Arabidopsis thaliana*; "Ω" refers to an Ω sequence of 5'-UTR derived from tobacco mosaic virus; "RdRp" refers to an RNA-dependent RNA polymerase derived from tobamovirus (turnip vein clearing virus); "MP" refers to a movement protein; "GFP" refers to a green fluorescence protein; "NTR" refers to a 3'-UTR derived from cr-TMV (crucifer-infecting tobamovirus); and "Nos-t" refers to a NOS terminator. In addition, the region indicated by a dotted box of "RdRp" and "MP" refers to an intron.

Eigher the pBYR2HS-EGFP vector or the GFP_pICH18711 vector was introduced into *Agrobacterium tumefaciens* GV3101 strains. Then, *Agrobacterium tumefaciens* was infected to 4- or 5-week-old *Nicotiana benthamiana* leaves.

After introduction of the vectors, each plant was incubated for 3 days to transiently express EGFP or GFP. Subsequently, each plant was irradiated with a blue LED, and the fluorescence of EGFP or GFP was observed using an ultraviolet absorbing filter (Model "SC-52", available from Fujifilm Corporation).

Figure 12A:
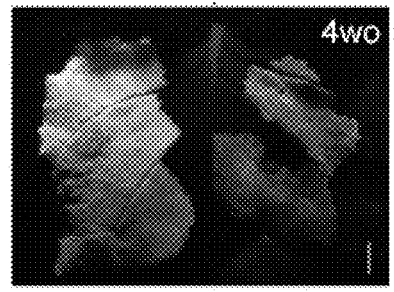
FIGS. 12A and B are photographs showing the results of observation of fluorescence of expressed EGFP or GFP in Experimental Example 6.
Figure 12B:
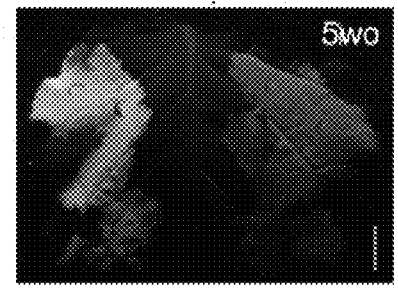

FIGS. 12A and 12B are photographs showing the results of observing the fluorescence of expressed EGFP or GFP. In FIGS. 12A and 12B, the scale bars indicate 1 cm length. FIG. 12A shows the results of 4-week-old *Nicotiana benthamiana* leaves, and FIG. 12B shows the results of 5-week-old *Nicotiana benthamiana* leaves. The vectors introduced are shown at the top of FIGS. 12A and 12B. In FIGS. 12A and 12B, "4wo" shows the result of 4-week-old leaves, and "5wo" shows the result of 5-week-old leaves.

As a result, in a case of using either 4- or 5-week-old *Nicotiana benthamiana* leaves, the expression level of EGFP or GFP tended to be higher in a case where the pBYR2HS-EGFP vector was introduced than in a case where the GFP_pICH18711 vector was introduced.

Subsequently, total soluble protein was prepared from the *Nicotiana benthamiana* leaves. Subsequently, the prepared protein corresponding to 0.2 mg fresh weight (FW) was subjected to SDS-polyacrylamide gel electrophoresis (SDS-PAGE) and the total soluble protein was detected by Coomassie Brilliant Blue (CBB) staining.

Figure 13A:
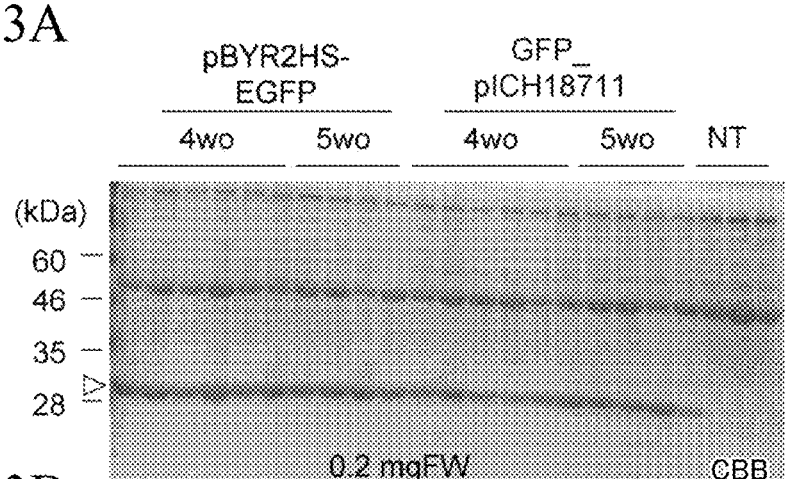
FIG. 13A is a photograph showing the results of CBB staining of SDS-PAGE gels of total soluble protein prepared from *Nicotiana benthamiana* leaves in Experimental Example 6.

FIG. 13A is a photograph showing the results of CBB staining of SDS-PAGE gels of total soluble protein prepared from *Nicotiana benthamiana* leaves. The vectors introduced are shown at the top of FIG. 13A. Further, in FIG. 13A, the arrowhead indicates an EGFP or GFP protein, "4wo" shows the result of 4-week-old leaves, and "5wo" shows the result of 5-week-old leaves. In addition, "NT" refers to a total soluble protein prepared from the *Nicotiana benthamiana* leaves into which no vector has been introduced.

Figure 13B:
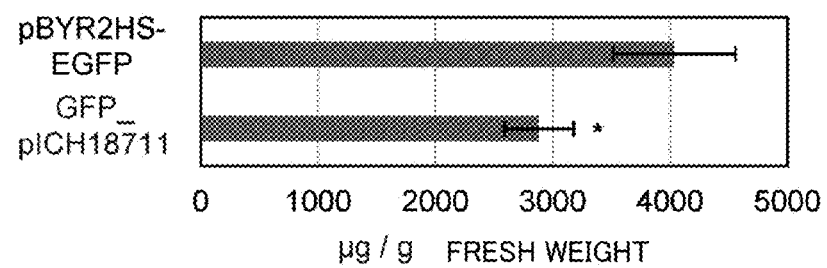
FIG. 13B is a graph in which the expression level of EGFP or GFP in FIG. 13A is quantified.

In addition, FIG. 13B is a graph in which the expression level of EGFP or GFP in FIG. 13A is quantified. The numerical values in the graph of FIG. 13B are shown as mean value±standard deviation of expression levels of EGFP or GFP in 4- and 5-week-old *Nicotiana benthamiana* leaves. In addition, in FIG. 13B, "*" indicates that there is a significant difference at $P<0.05$ as a result of a Student's t-test.

As a result, it was demonstrated that the expression level of a protein was significantly higher in a case where the pBYR2HS-EGFP vector was introduced than in a case where the GFP_pICH18711 vector was introduced. This result indicates that the expression level of a protein by the pBYR2HS-EGFP vector was higher than the expression level of a protein by the magnICON system.

INDUSTRIAL APPLICABILITY

According to the present invention, it is possible to provide an expression system that can be applied to plants other than those belonging to the genus *Nicotiana* and exhibits a high expression level of a protein.

The invention claimed is:

1. An expression system for producing a target protein of interest in a plant, comprising:
   (a) first nucleic acid fragment comprising;
      a long intergenic region (LIR) derived from geminivirus,
      a small intergenic region (SIR) derived from geminivirus, and
      an expression cassette of a target protein linked between the LIR and the SIR, said expression cassette consisting essentially of;
      a promoter,
      a nucleic acid fragment encoding the target protein, and
      two operably linked terminators in this order; and
   (b) a second nucleic acid fragment comprising an expression cassette of a Rep/RepA protein derived from geminivirus, wherein
   the two operably linked terminators are selected from the group consisting of:
      (i) a terminator derived from *Arabidopsis thaliana* heat-shock protein 18.2 gene and a tobacco extensin gene terminator, wherein expression of the target protein of interest is increased by at least 1.6 fold as compared with a system using said *Arabidopsis thaliana* heat-shock protein 18.2 gene terminator alone, by at least 2.1 fold as compared with a system using said tobacco extensin gene terminator alone, and by at least 1.3 fold as compared with a system using three terminators comprising said terminator from *Arabidopsis thaliana* heat-shock protein 18.2 gene, and said tobacco extensin gene terminator and a 35S terminator; and
      (ii) a terminator derived from *Arabidopsis thaliana* heat-shock protein 18.2 gene and a terminator derived from *Arabidopsis thaliana* heat-shock protein 18.2 gene, wherein expression of the target protein of interest is increased by at least 1.4 fold as compared with a magnICON expression system, and by at least 1.2 fold as compared with the system using said three terminators of part (i), and the plant is selected from the group consisting of a solanaceous plant, an *Asteraceae* plant, a cucurbitaceous plant and an orchidaceous plant.

2. The expression system according to claim 1, further comprising: a third nucleic acid fragment comprising an expression cassette of a gene-silencing suppressor.

3. The expression system according to claim 2, wherein the gene-silencing suppressor is a gene-silencing suppressor P19 derived from tomato bushy stunt virus.

4. The expression system according to claim 2, wherein the first nucleic acid fragment, the second nucleic acid fragment, and the third nucleic acid fragment are present in a single vector.

5. The expression system according to claim 4, further comprising:
   a T-DNA right border sequence (RB); and
   a T-DNA left border sequence (LB),
   and wherein the first nucleic acid fragment, the second nucleic acid fragment, and the third nucleic acid fragment are present between the RB and the LB.

6. The expression system according to claim 1, wherein said geminivirus is a bean yellow dwarf virus.

7. A method for producing a target protein of interest in a plant cell comprising: introducing the expression system according claim 1 into a plant cell, expressing the target protein of interest and isolating the target protein of interest from the plant cell expressing said target protein of interest.

8. The expression system according to claim 1, wherein the first nucleic acid fragment and the second nucleic acid fragment are operably linked and present in a single vector.

9. The expression system according to claim 1, wherein the first nucleic acid fragment and the second nucleic acid fragment are separately present as independent nucleic acid fragments in the expression system.

* * * * *